(12) United States Patent
Del Río Zambrana et al.

(10) Patent No.: US 7,351,732 B2
(45) Date of Patent: Apr. 1, 2008

(54) CYCLOALKANEDIONE DERIVATIVES, METHOD FOR THE PRODUCTION THEREOF AND THEIR PHARMACOLOGICAL APPLICATIONS

(75) Inventors: Joaquin Del Río Zambrana, Pamplona (ES); Diana Frechilla Manso, Pamplona (ES); M. Luz López Rodríguez, Madrid (ES); Bellinda Benhamú Salama, Alcobendas (ES); José Ángel Fuentes Cubero, Madrid (ES); Mercedes Delgado Wallace, Majadahonda (ES)

(73) Assignee: Schwarz Pharma S.L., Monhelm (DE)

( * ) Notice: Subject to any disclaimer, the term of this patent is extended or adjusted under 35 U.S.C. 154(b) by 125 days.

(21) Appl. No.: 10/522,697

(22) PCT Filed: Jul. 29, 2003

(86) PCT No.: PCT/ES03/00394

§ 371 (c)(1),
(2), (4) Date: Jan. 27, 2005

(87) PCT Pub. No.: WO2004/014915

PCT Pub. Date: Feb. 19, 2004

(65) Prior Publication Data

US 2005/0250777 A1    Nov. 10, 2005

(30) Foreign Application Priority Data

Jul. 31, 2002  (ES) ................................ 200201811

(51) Int. Cl.
*A61K 31/4184* (2006.01)
*A61K 31/429* (2006.01)
*A61K 31/427* (2006.01)
*C07D 235/02* (2006.01)
*C07D 235/04* (2006.01)
*C07D 513/04* (2006.01)
*C07D 277/34* (2006.01)

(52) U.S. Cl. ..................... 514/387; 514/368; 514/369; 514/373; 548/302.7; 548/207; 548/154; 548/183

(58) Field of Classification Search ............... 548/183, 548/302.7, 303.7; 514/369, 387, 38
See application file for complete search history.

(56) References Cited

U.S. PATENT DOCUMENTS

| | | | | |
|---|---|---|---|---|
| 4,055,410 A | * | 10/1977 | Cheng | ......................... 504/266 |
| 5,137,901 A | | 8/1992 | Junge et al. | |
| 6,919,360 B2 | | 7/2005 | Scherling et al. | |

FOREIGN PATENT DOCUMENTS

| | | |
|---|---|---|
| EP | 0352613 B1 | 4/1994 |
| EP | 1674103 A1 | 6/2006 |
| ES | 2052829 A | 4/1994 |
| ES | 2052829 T3 | 7/1994 |
| ES | 2082727 A1 | 3/1996 |
| ES | 2094690 A1 | 1/1997 |
| ES | 2109190 A1 | 1/1998 |
| ES | 2129370 A1 | 6/1999 |
| ES | 2154605 A1 | 4/2001 |
| ES | 2199086 A1 | 2/2004 |
| ES | 2238015 A1 | 8/2005 |
| WO | WO 9606846 A1 | 3/1996 |
| WO | WO 9735860 A1 | 10/1997 |
| WO | WO 9915527 A1 | 4/1999 |
| WO | WO 9929687 A1 | 6/1999 |
| WO | WO 03029250 A1 | 4/2003 |
| WO | WO 2004014915 A1 | 2/2004 |
| WO | WO 2005075480 A1 | 8/2005 |
| WO | WO 2006069993 A1 | 7/2006 |

OTHER PUBLICATIONS

International Preliminary Examination Report for PCT Application No. PCT/ES2003/000394.
Ambrossio, E. et al., [$^3$ H]prazosin binding to central nervous system regions of male and female rats, Neurosci. Lett. 49(1-2):193-197 (1984).
Titeler, M. et al., *Selectivity of serotonergic drugs for multiple brain serotonin receptors: Role of [$^3$ H]-4-bromo-2,5-dimethoxylphenylisopropylamine ( [$^3$ H]DOB ), A 5-HT$_2$ agonist radioligand*, Biochem. Pharmacol. 36(19):3265-3271 (1987).

(Continued)

Primary Examiner—Rebecca Anderson
Assistant Examiner—Jason M Nolan
(74) Attorney, Agent, or Firm—Harness, Dickey & Pierce PLC; J. Timothy Keane

(57) ABSTRACT

New cycloalkanedione derivatives that are serotonin (5-hydroxytriptamine, 5-HT) 5-HT$_{1A}$ receptor subtype agonists and, consequently, they are useful in the treatment of pathological states for which an agonist of these receptors is indicated.

They are particularly useful as neuroprotective agents, of special interest in the treatment and prophylaxis of cerebral damage produced by traumatic or ischemic stroke.

In general terms, said cycloalkanedione derivatives correspond to formula I:

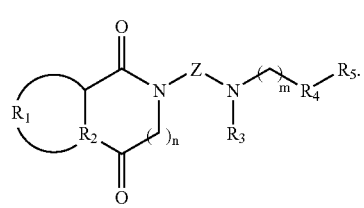

23 Claims, No Drawings

OTHER PUBLICATIONS

Wong, D.T. et al., *Specific [³H]LY278584 binding to 5-HT₃ recognition sites in rat cerebral cortex*, Eur. J. Pharmacol. 166(1):107-110 (1989).

Clark, R.D. et al., *1,9OALkano-Bridged 2,3,4,5-Tetrahydro-1H-3-benzazepines with affinity for the $a_2$-adrenoceptor and the 5-$HT_{1a}$ receptor*, J. Med. Chem. 33(2):633-641 (1990).

Grossman, C.J. et al.,*Development of a radioligand binding assay for 5-$HT_4$ receptors in guinea-pig and rat brain*, Br. J. Pharmacol. 109:618-624 (1993).

De Vry, J., *5-HT1A receptor agonists: recent developments and controversial issues*, Psychopharmacology 121(1):1-16 (1995).

Koh, J.Y. et al., *Potentiated necrosis of cultured cortical neurons by neurotrophins*, Science 268(5210):573-575 (1995).

Koroshetz, W.J. and Moskowitz, M.A., *Emerging treatments for stroke in humans*, Trends Pharmacol. Sci. 17(6):227-33 (1996).

Lopez-Rodriguez, M.L. et al., *Novel benzimidazole-4-carboxylic acid derivatives as potent and selective 5-$HT_3$ receptor ligands*, Bioorg. Med. Chem. Lett.6(11): 1195-1198 (1996).

Lopez-Rodriguez, M.L. et al., *Synthesis and structure-activity relationships of a new model of arylpiperazines. 1. 2-[[4-(o-methoxphenyl)piperazin-1-yl]methyl]-1,3-dioxoperhydroimidazo[1,5-alpha]pyridine: a selective 5-$HT_{1A}$ receptor agonist*, J. Med. Chem. 39(22):4439-4450 (1996).

Lopez-Rodriguez, M.L. et al., *2-[4-(o-Methoxyphenyl)piperazin-1-ylmethyl]-1,3-dioxoperhydroimidazo[1,5-a]pyridine as a new selective 5-$HT_{1A}$ receptor ligand*, Bioorg. Med. Chem. Lett. 6(6):689-694 (1996).

Matsuyama, S. et al., *Regulation of glutamate release via NMDA and 5-$HT_{1A}$ receptors in guinea pig dentate gyrus*, Brain Res. 728(2):175-180 (1996).

Lopez-Rodriguez, M.L. et al., *Comparative receptor mapping of serotoninergic 5-$HT_3$ and 5-$HT_4$ binding sites*, J. Comput.-Aided Mol. Des. 11(6):589-599 (1997).

Lopez-Rodriguez, M.L. et al., *Synthesis and structure-activity relationships of a new model of arylpiperazines. 2. Three-dimensional quantitative structure-activity relationships of hydantoin-phenylpiperazine derivatives with affinity for 5-HT1A and alpha 1 receptors. A comparison of CoMFA models*, J. Med. Chem. 40(11):1648-1656 (1997).

Lopez-Rodriguez, M.L. et al., *Synthesis and structure-activity relationships of a new model of arylpiperazines. 3.1 2-[omega-(4-arylpiperazin-1-yl)alkyl]perhydropyrrolo-[1,2-c]imidazoles and—perhydroimidazo[1,5-a]pyridines: study of the influence of the terminal amide fragment on 5-HT1A affinity/selectivity*, J. Med. Chem. 40(16):2653-2656 (1997).

Aguirre, N. et al., *MDMA ('Ecstacy') enhances5-$HT_{1a}$ receptor density and 8-OH-DPAT-induced hypothermia: Blockade by drugs preventing 5-hydroxytryptamine depletion*, Eur. J. Pharmacol. 346(2-3):181-188 (1998).

Beneytez, M.E. et al., *Preclinical pharmacology of B-20991, a 5-$HT_{1A}$ receptor agonist with anxiolytic activity*, Eur. J. Pharmacol. 344:127-135(1998).

Lopez-Rodriguez, M.L. et al., *1-[ω-(4-Arylpiperazin-1-yl)alkyl]3-diphenylmethylene-2,5-pyrrolidinediones as 5-$HT_{1A}$ receptor ligands: Study of the steric requirements of the terminal amide fragment on 5-$HT_{1A}$ affinity/selectivity*, Bioorg. Med. Chem. Lett. 8:581-586 (1998).

Nonaka, S. et al., *Chronic lithium treatment robustly protects neurons in the central nervous system against excitoxicity by inhibiting N-methyl-D-aspartate receptor-mediated calcium influx*, Proc. Nat'l. Acad. Sci. USA 95(5):2642-2647 (1998).

Suchanek, B. et al., *The 5-$HT_{1A}$ receptor agonist BAY ×3702 prevents staurosporine-induced apoptosis*, Eur. J. Pharmacol. 355(1):95-101 (1998).

Ahlemeyer B. et al., *The 5-$HT_{1A}$ receptor agonist Bay ×3702 inhibits apoptosis induced by serum deprivation in cultured neurons*, Eur. J. Pharmacol. 370(2):211-216 (1999).

Justicia, C. and Planas, A.M., *Transforming growth factor-αacting at the epidermal growth factor receptor reduces infarct volume after permanent middle cerebral artery occlusion in rats*, J. Cereb. Blood Flow Metab. 19(2):128-132 (1999).

Lopez-Rodriguez, M.L. et al., *Benzimidazole derivatives. 1. Synthesis and structure-activity relationships of new benzimidazole-4-carboxamides and carboxylates as potent and selective 5-$HT_4$ receptor antagonists*, Bioorg. Med. Chem. 7:2271-2281 (1999).

Lopez-Rodriguez, M.L. et al., *Benzimidazole derivatives. 2. Synthesis and structure-activity relationships of new azabicyclic benzimidazole-4-carboxylic acid derivatives with affinity for serotoninergic 5-$HT_3$ receptors*, J. Med. Chem. 42:5020-5028(1999).

Lopez-Rodriguez, M.L. et al., *Design and synthesis of 2-[4-[4-((m--(ethylsulfonamido)phenyl)piperazin-1-yl]butyl]-1,3-dioxoperhydropyrrolo[1,2-c]imidazole (EF-7412)using neural networks. A selective derivative with mixed 5-$HT_{1A}/D_2$ antagonist properties*, Bioorg. Med. Chem. Lett. 9:1679-1682(1999).

Lopez-Rodriguez, M.L. et al., *Synthesis and structure-activity relationships of a new model of arylpiperazines. 4. 1-[omega-(4-Arylpiperazin-1-yl)alkyl]-3-(diphenylmethylene) -2,5-pyrrolidinediones and -3-(9H-fluoren-9-ylidene)-2,5-pyrrolidinediones: study of the steric requirements of the terminal amide fragment on 5-$HT_{1A}$ affinity/selectivity*, J. Med. Chem. 42(1):36-49 (1999).

Lopez-Rodriguez, M.L. et al., *Synthesis of new (benzimidazolyl)piperazines with affinity for the 5-$HT_{1A}$ receptor via Pd(0) amination of bromobenzimidazoles*, Bioorg. Med. Chem. Lett. 9:2339-2342, 1999.

Galter, D. et al., *Sequential activation of the 5-$HT_{1A}$serotonin receptor and TrkB induces the serotonergic neuronal phenotype*, Mol. Cell. Neurosci. 15(5):446-455 (2000).

Lopez-Rodigueiz, M.L. et al., *First pharmacophoric hypothesis for 5-$HT_7$ antagonism*, Bioorg. Med. Chem. Lett. 10:1097-1100(2000).

Lopez-Rodriguez, M.L. et al., *Pd(0) Amination of benzimidazoles as an efficient method towards new (benzimidazolyl)piperazines with high affinity for the 5-$HT_{1A}$ receptor*, Tetrahedron 56:3245-3253 (2000).

Schaper, C. et al., *Stimulation of 5-$HT_{1A}$ receptors reduces apoptosis after transient forebrain ischemia in the rat*, Brain Res. 883(1): 41-50 (2000).

Torup, L. et al., *Neuroprotective effect of 8-OH-DPAT in global cerebral ischemia assessed by stereological cell counting*, Eur. J. Pharmacol. 395(2):137-141 (2000).

Kline, A.E. et al., *The selective 5-$HT_{1A}$ receptor agonist repinotan HCl attenuates histopathology and spatial learning deficits following traumatic brain injury in rats*, Neuroscience 106(3) 547-555 (2001).

Lopez-Rodriguez, M.L. et al., *Computational model of the complex between GR113808 and the 5-$HT_4$ receptor guided by site-directed mutagenesis and the crystal structure of rhodopsin*, J. Comput.-Aided. Mol. Des. 15: 1025-1033 (2001).

Lopez-Rodriguez, M.L. et al., *Study of the bioactive conformation of novel 5-$HT_4$ receptor ligands: influence of an intramolecular hydrogen bond*, Tetrahedron 57:6745-6749 (2001).

Lopez-Rodriguez, M.L. et al., *Synthesis and structure-activity relationships of a new model of arylpiperazines. 5. Study of the physicochemical influence of the pharmacophore on 5-HT(1a)/ alpha(1)-adrenergic receptor affinity: synthesis of a new derivative with mixed 5-HT (1a)/d(2) antagonist properties*, J. Med. Chem. 44(2):186-197 (2001).

Lopez-Rodriguez, M.L. et al., *Synthesis and structure-activity relationships of a new model of arylpiperazines.6. Study of the 5-HT(1a)/alpha(1)-adrenergic receptor affinity by classical hansch analysis, artificial neural networks, and computational simulation of ligand recognition*, J. Med. Chem. 44(2):198-207 (2001).

Lopez-Rodriguez, M.L. et al., *3D-QSAR/CoMFA and recognition models of benzimidazole derivatives at the 5-$HT_4$ receptor* Bioorg. Med. Chem. Lett. 11:2807-2811 (2001).

Mauler, F., et al., *Inhibition of evoked glutamate release by the neuroprotective 5-$HT_{1A}$ receptor agonist BAY×3702 in vitro and in vivo*, Brain Res. 888(1):150-157 (2001).

Caicoya, A.G. et al., *Biochemical, electrophysiological and neurohormonal studies with B-20991, a selective 5-$HT_{1A}$ receptor agonist*, Pharmacology 62: 234-242 (2001).

Lopez-Rodriguez, M.L. et al., *Arylpiperazine derivatvies acting at 5-$HT_{1A}$ receptors*, Curr. Med. Chem. 9:443-469 (2002).

Lopez-Rodriguez, M.L. et al., *Benzimidazole derivatives. 3. 3D-QSAR/CoMFA model and computational simulation for the recognition 5-HT$_4$ receptor antagonists*, J. Med. Chem. 45: 4806-4815 (2002).

Lopez-Rodriguez, M.L. et al., *Design, synthesis and pharmacological evaluation of 5-hydroxytryptamine$_{1a}$ receptor ligands to explore the three-dimensional structure of the receptor*, Mol. Phamacol. 62:15-21 (2002).

Lopez-Rodriguez, M.L. et al., *5-HT$_4$ receptor antagonists: structure-affinity relationships and ligand-receptor interactions*, Curr. Topics Med. Chem. 2:625-641 (2002).

Lopez-Rodriguez, M.L. et al., *Benzimidazole derivatives. 4. The recognition of the voluminous substituent attached to the basic amino group of 5-HT$_4$ receptor antagonists*, J. Comput.-Aided Mol. Des. 17:515-524 (2003).

Lopez-Rodriguez, M.L. et al., *Design and synthesis of new benzimidazole-arylpiperazine derivatives acting as mixed 5-HT$_{1A}$/5-HT$_3$ ligands*, Bioorg. Med. Chem. Lett. 13:3177-3180 (2003).

Lopez-Rodriguez, M.L. et al., *Design and synthesis of S-(-)-2-[[4-(napht-1-yl)piperazin-1-yl]methyl]-1,4-dioxoperhydropyrrolo[1,2-a]pyrazine(CSP-2053) using computational simulation. A 5-HT$_{1A}$ receptor agonist*, Bioorg. Med. Chem. Lett. 13(8):1429-1432 (2003).

Lopez-Rodriguez, M.L. et al., *Optimization of the pharmacophore model for 5-HT$_7$ receptor antagonism. Design and synthesis of new naphtholactam and naphthosultam derivatives*, J. Med. Chem. 46:5638-5650 (2003).

Pascual D. et al., *New benzimidazole derivatives: selective and orally active 5-HT$_3$ receptor antagonists*, Eur. J. Pharmacol. 462:99-107 (2003).

Lopez-Rodriguez, M.L. et al., *Benzimidazole derivatives. 5. Design and synthesis of new benzimidazole-arylpiperazine derivatives acting as mixed 5-HT$_{1A}$/5-HT$_3$ ligands*, Bioorg. Med. Chem. 12:5181-5191 (2004).

Lopez-Rodriguez, M.L. et al., *Serotonin 5-HT$_7$ receptor antagonists*, Curr. Med. Chem.-CNSA 4:203-214 (2004).

Lopez-Rodriguez, M.L. et al., *Synthesis and structure-activity relationships of a new model of arylpiperazines. Part 7: Study of the influence of lipophilic factors at the terminal amide fragment on 5-HT$_{1A}$ affinity/selectivity*, Bioorg. Med. Chem. 12(6):1551-1557 (2004).

Delgado, M. et al., *Anxiolytic-like effect of a serotonergic ligand with high affinity for 5-HT$_{1A}$, 5-HT$_{2A}$ and 5-HT$_3$ receptors*, Eur. J. Pharmacol. 511:9-19 (2005).

Lopez-Rodriguez, M.L. et al., *A three-dimensional pharmacophore model for 5-hydroxytryptamine$_6$ (5-HT$_6$)receptor antagonists*, J. Med. Chem. 48:4216-4219 (2005).

Lopez-Rodriguez, M.L. et al., *Synthesis and structure-activity relationships of a new model of arylpiperazines. 8. Computational simulation of ligand-receptor interaction of 5-HT$_{1A}$R agonists with selectivity over alpha1-adrenoceptors*, J. Med. Chem. 48(7):2548-2558 (2005).

\* cited by examiner

CYCLOALKANEDIONE DERIVATIVES, METHOD FOR THE PRODUCTION THEREOF AND THEIR PHARMACOLOGICAL APPLICATIONS

PRIORITY CLAIM TO RELATED PATENT APPLICATIONS

This patent application claims priority (as a U.S. national phase application filed under 35 U.S.C. §371) to International Patent Application No. PCT/ES03/00394 (filed Jul. 29, 2003), which, in turn, claims priority to Spanish Patent Application No. P 200201811 (filed Jul. 31, 2002). The entire content of each of these priority patent applications is incorporated by reference into this patent application.

TECHNICAL FIELD OF THE INVENTION

The present invention relates to new chemical compounds, their preparation, pharmaceutical formulations that contain them and their use in medicine, the present invention particularly relating to new cycloalkanedione derivatives which are serotonin (5-hydroxytriptamine, 5-HT) $5\text{-HT}_{1A}$ receptor subtype agonists. Therefore, they are useful in the treatment of pathological states for which an agonist of these receptors is indicated.

In particular, the compounds of the present invention are useful as neuroprotective agents, which confers them a special interest in the treatment and prophylaxis of cerebral damage due to traumatic or ischemic stroke.

BACKGROUND OF THE INVENTION

The pharmacological possibilities for the treatment of acute cerebral stroke are very limited; until now, only thrombolitic therapy using a tissue plasminogen activator (tPA) can be moderately effective. Although the primary cellular damage caused by ischemia is not susceptible to treatment, there is the possibility of acting on secondary neuronal death in the penumbra zone, where a series of processes extending the damage occurs. Amongst them, particular attention has been paid to massive release of excitatory amino acids, and in this sense, drugs that prevent glutamate release, glutamate receptor antagonists, both NMDA and AMPA receptors, are effective in different experimental models.

At present, 14 different subtypes of serotonergic receptors are known. The $5\text{-HT}_{1A}$ receptors, the localization thereof being both presynaptic and postsynaptic, are the target of a group of anxiolytic drugs and perhaps they are also involved in the actions of specific anti-depressant drugs.

In ES 2052829 substituted aminoethyl tetralins and analogous heterocyclics are disclosed as selective agonists of the $5\text{-HT}_{1A}$ subtype serotonergic receptors. One of the products disclosed in said document, BAYx3702, has shown experimentally, both in vitro (Suchanek et al., 1998; Ahlemeyer et al., 1999) and in vivo (Schaper et al., 2000; Torup et al., 2000; Kline et al., 2001), its neuroprotective effect due to its agonist action on the $5\text{-HT}_{1A}$ receptor.

Spanish patent application No. 200102113, of the same authors of the present invention, discloses a series of compounds that behave as pure $5\text{-HT}_{1A}$ receptor agonists although with only moderate potency, wherein neuroprotective action of this series of compounds could only be demonstrated using primary rat neuronal cultures.

The neuroprotective effect of the $5\text{-HT}_{1A}$ receptor agonists may be due to different mechanisms amongst which the hyperpolarization in the activation of $K^+$ channels, glutamate release inhibition (Matsuyama et al., 1996; Mauler et al., 2001) and the increase in BDNF neurotrophin expression (Galter et al. 2000) are highlighted.

The aforementioned data enables prediction of a new application for the compounds capable of activating the $5\text{-HT}_{1A}$ receptors, namely, their use in the treatment of cerebral damage associated with ischemialhypoxia processes or traumatic incidents. Therefore, it is of great interest to have new agonist compounds of serotonergic $5\text{-HT}_{1A}$ receptors which have neuroprotective effects and which can provide efficient treatment against cerebral damage associated with ischemialhypoxia processes or cranium-brain traumatic injuries.

No admission is made that any reference (or any portion of any reference) discussed above is prior art.

DESCRIPTION OF THE INVENTION

The present invention, as indicted in the heading, relates to new cycloalkanedione derivatives, their preparation process and their pharmacological applications.

In a first aspect of the present invention, said cycloalkanedione derivatives are characterized in that they correspond to the general formula I:

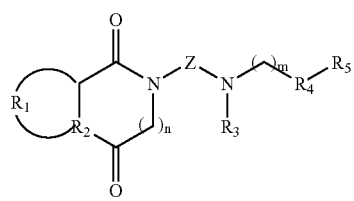

where:
$R_1$ is selected from the group formed by H, —(CH$_2$)$_3$—, —(CH$_2$)$_4$—, —CH$_2$—S—CH$_2$—, —S—CH$_2$—CH$_2$—;
$R_2$ is selected from the group formed by N, S;
n has a value of 0 or 1;
Z is selected from the group formed by C2-C10-alkyl, C2-C10-alkenyl, C2-C10-alkinyl;
$R_3$ is selected from the group formed by H, C1-C10-alkyl, aryl, aralkyl;
m has a value of 0 to 2;
$R_4$ is selected from the group formed by O, CH$_2$;
$R_5$ is selected from the group formed by:

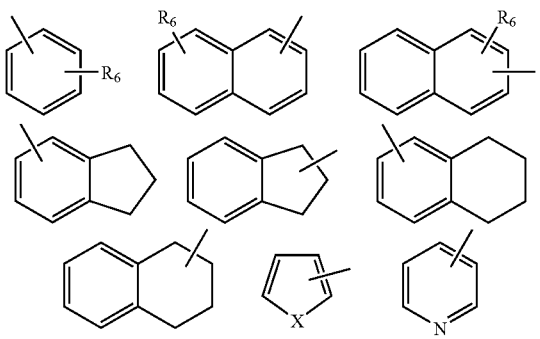

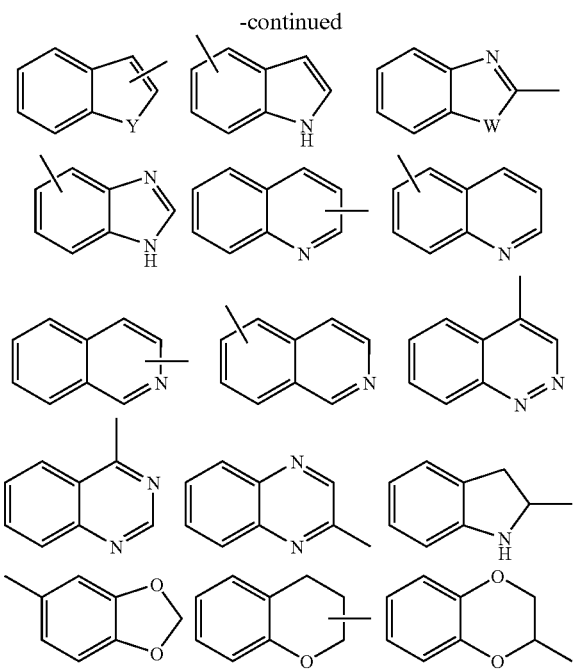

where:
$R_6$ is selected from the group formed by H, C1-C5-alkyl, C1-C5-alkoxyl, OH, F, Cl, Br, I;
X is selected from the group formed by O, S, NH, $NCH_3$;
Y is selected from the group formed by O, NH;
W is selected from the group formed by S, NH.

In a preferred embodiment of the present invention, the formula (I) compounds are those where: Z represents a C2-C10-alkyl group, and $R_5$ is selected from the group formed by:

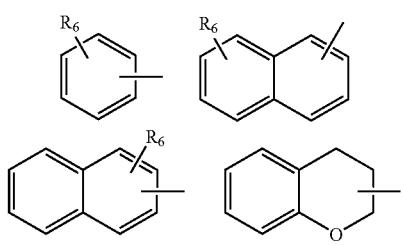

where the definitions of $R_1$, $R_2$, $R_3$, n, m, $R_4$ and $R_6$ are identical to those previously made.

Even more preferred are formula (I) compounds where: Z is butyl, $R_3$ is H, and $R_5$ is selected from the group formed by:

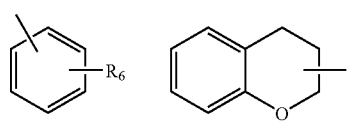

where the definitions of $R_1$, $R_2$, n, m, $R_4$ and $R_6$ are identical to those previously made.

Unless otherwise indicated, the alkyl groups referred to in the present invention, as well as the alkyl residues of other groups referred to in the present invention (e.g. alkoxyl), can be linear or branched, and can also be cyclic (e.g. cyclopropyl, cyclobutyl, cyclopentyl or cyclohexyl), or linear or branched and contain these cyclic residues.

Unless otherwise indicated, the alkenyl groups referred to in the present invention are linear (e.g. 1-propenyl, 2-butenyl) and their isomeric forms.

Unless otherwise indicated, the alkynyl groups referred to in the present invention are linear (e.g. 2-butynyl).

The term aryl includes any monocyclic aromatic group containing between 5 and 12 carbon atoms, optionally interrupted by one or several heteroatoms selected from N, O or S.

The term aralkyl refers to an aryl group bonded to a previously defined alkyl group, such as benzyl or phenethyl.

In the scope of the present invention, the compounds according to the invention may have several asymmetric carbon atoms and, therefore, have various stereochemical forms. The compounds according to the invention may also be in the form of their salts. In general, their salts wish inorganic or organic acids can be mentioned.

In the scope of the present invention, those salts which are physically compatible will be preferable. Particularly preferable are, for example, the salts with hydrochloric acid, hydrobromic acid, sulphuric acid, phosphoric acid, methane sulphonic acid, ethane sulphonic acid, o-toluene sulphonic acid, m-toluene sulphonic acid, p-toluene sulphonic acid, benzene sulphonic acid, o-naphthalene sulphonic acid, m-naphthalene sulphonic acid, p-naphthalene sulphonic acid, acetic acid, propionic acid, lactic acid, oxalic acid, malonic acid, succinic acid, maleic acid, fumaric acid, malic acid, tartaric acid, citric acid or benzoic acid.

The compounds with potent agonist action on the 5-$HT_{1A}$ receptor disclosed in the present invention represent, therefore, effective products to treat diseases of the central nervous system which include anxiety disorders, different forms of depression and mixed disorders of anxiety-depression such as obsessive compulsive disorders, phobias, bulimia, etc. They are also suitable for prophylaxis and treatment of neuronal damage in episodes of cerebral infarction, in promoting the survival of cells located in the penumbra zone surrounding the ischemic focus.

The new active products can be transformed in a known manner in usual formulations, such as tablets, coated tablets, capsules, pills, granulates, micro-granules, aerosols, syrups, emulsions, suspensions and solutions, with the use of pharmaceutically suitable, non-toxic, inert excipients or solvents. In this case, the therapeutically active compound should be present in a concentration of approximately 0.5 to 90% by weight of the total mixture, i.e. in sufficient quantities to attain the indicated dosage range.

The compounds herein disclosed are pure serotonergic 5-$HT_{1A}$ receptor agonists, which have been demonstrated by appropriate functional studies. Consequently, the compounds subject of the present invention have a protective effect on the neuronal death of an apoptotic or necrotic character induced by serum deprivation or by glutamate in neuronal cultures.

According to another aspect of the present invention, two alternative processes are provided to prepare the compounds of general formula I: by reaction of intermediate halogen derivatives II (L=Cl, Br) with suitable amines III in acetonitrile as reaction solvent (Scheme I below), or by reaction of intermediate amines IV with appropriate halogen derivatives V (L=Cl, Br) in acetonitrile as reaction solvent (Scheme II below).

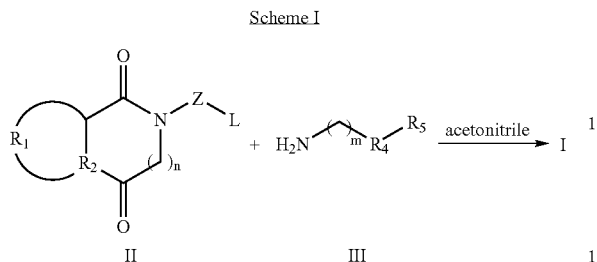

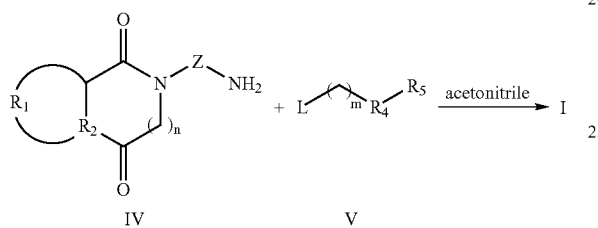

The compounds with $R_3$ different from H are produced by alkylation of the analogues wherein $R_3$ is hydrogen.

The definitions of $R_1$, $R_2$, n, Z, m, $R_4$ and $R_5$ in these schemes are identical to those made previously for the products of the invention.

The formula II intermediates are obtained by the reaction of hydantoin, diketopiperazine or cyclic imide with the appropriate halogen derivative in the presence of sodium hydride and N,N-dimethylformamide as a reaction solvent, as represented in Scheme III.

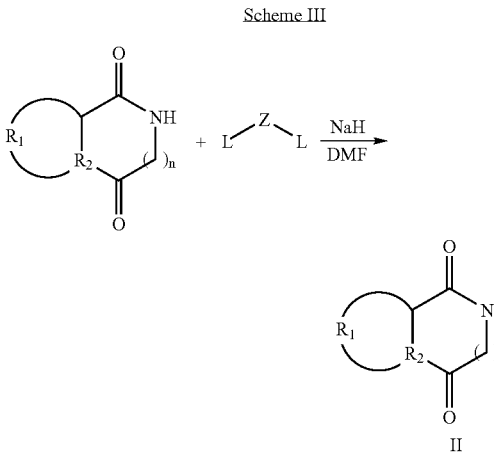

The formula IV intermediates are obtained by reaction of hydantoin, diketopiperazine or cyclic imide with the appropriate halonitrile in the presence of sodium hydride and N,N-dimethylformamide as reaction solvent, and subsequent catalytic hydrogenation, as represented in Scheme IV.

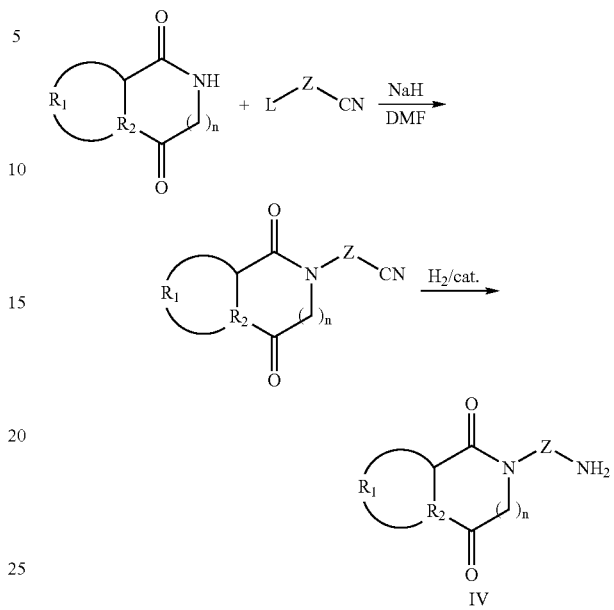

Some of the intermediates III and V are commercial. It is also possible to obtain said intermediates following procedures disclosed in the literature or by conventional synthetic routes.

The final products have been structurally characterized by techniques of IR, NMR and quantitative elemental analysis. For easier handling, when the final product is not crystalline it is transformed in a pharmaceutically acceptable salt, derived from an inorganic or organic acid.

The in vitro affinity of the compounds of general formula I in the 5-$HT_{1A}$, 5-$HT_{2A}$, 5-$HT_3$, 5-$HT_4$, 5-$HT_7$, $\alpha_1$ and $D_2$ cerebral receptors have been evaluated by radioligand displacement tests. The following specific ligands and tissues have been used:

(a) 5-$HT_{1A}$ receptors, [$^3$H]-8-OH-DPAT, rat cerebral cortex;
(b) 5-$HT_{2A}$ receptors, [$^3$H]ketanserin, rat cerebral cortex;
(c) 5-$HT_3$ receptors, [$^3$H]LY 278584, rat cerebral cortex;
(d) 5-$HT_4$ receptors, [$^3$H]GR 113808, rat striatum;
(e) 5-$HT_7$ receptors, [$^3$H]-5-CT, rat hypothalamus;
(f) $\alpha_1$ receptors, [$^3$H]prazosin, rat cerebral cortex;
(g) $D_2$ receptors, [$^3$H]spiperone, rat striatum.

The functional character (agonist/antagonist) of the compounds of the present invention, has been studied in vitro by determining the inhibition of the stimulating effect of forskolin on adenylate cyclase in a cell line transfected with the 5-$HT_{1A}$ receptor, occasionally comparing the effect obtained with the [$^{35}$S]GTPγS fixation test to coronal sections of rat brain as well as the hyperpolarizing effect in the hippocampal area CA1, and further studying, in vivo, the 5-$HT_{1A}$ agonist character of the new compounds by analysis of the typical behavioural effects as well as of the hypothermia, and evaluating the prevention of these effects by the selective antagonist WAY-100635.

Furthermore, the neuroprotective activity of the compounds disclosed in the present invention has been studied, considering their capacity to prevent cell death, of a necrotic or apoptotic nature, in primary neuronal cultures and studying in vivo the prevention of neuronal death in the hippocampal area CA1 of gerbils after transient global ischemia as well as the reduction in volume of cerebral infarction after permanent occlusion in the middle cerebral artery in rats.

The present invention is illustrated with the following non-limitative examples.

EXAMPLES

Example 1

Synthesis of the Compounds of General Formula I

General Process.

To 1.5 mmol of intermediate amine III or IV dissolved in 2 mL of acetonitrile, a solution of 1.0 mmol of halogen derivative II or V in 1.5 mL of acetonitrile is added dropwise. The reaction mixture is heated to 60° C. with stirring during 6-24 hours (t.l.c.). After cooling, the solvent is removed at reduced pressure, the residue is dissolved in methylene chloride (20 mL) and is washed with an aqueous solution of 20% potassium carbonate. Next, the organic phase is dried over anhydrous $Na_2SO_4$ and the solvent is removed at reduced pressure. The resulting oil is purified by silica gel column chromatography, obtaining the final product in the form of a free base. The compound is isolated in the form of a hydrochloride and purified by recrystallization. The IR and NMR spectroscopic data correspond to the free base.

(±)-2-[4-[(Chroman-2-yl)methylamine]butyl]-1,3-dioxoperhydropyrrolo[1,2-c]imidazol, 1

Chromatography: toluene/methanol, 9:1. Yield: 35%. IR ($CHCl_3$, $cm^{-1}$): 1772, 1709, 1581, 1489, 1443. $^1$H-NMR ($CDCl_3$, δ): 1.47-1.86 (m, 5H), 1.91-2.12 (m, 4H), 2.16-2.34 (m, 1H), 2.64-2.92 (m, 6H), 3.16-3.28 (m, 1H), 3.48 (t, J=7.1 Hz, 2H), 3.66 (dt, J=11.2; 7.3 Hz, 1H), 4.05 (dd, J=9.1; 7.3 Hz, 1H), 4.11-4.18 (m, 1H), 6.81(t, J=7.6 Hz, 2H), 7.00-7.10 (m, 2H). $^{13}$C-NMR ($CDCl_3$, δ): 24.6; 25.6; 25.8; 26.9; 27.1; 27.5; 38.7; 45.4; 49.3; 54.1; 63.2; 75.0; 116.7; 120.1; 121.9; 127.1; 129.4; 154.5; 160.8; 173.9. Analysis calculated for $C_{21}H_{24}N_2O_4S.HCl$: C, 57.72; H, 5.77; N, 6.41, found: C, 57.64; H, 5.96; N, 6.19.

Example 2

(±)-2-[4-[(Chroman-2-yl)methylamine]butyl]-1,3-dioxoperhydroimidazo[1,5-b]thiazol, 2

Chromatography: toluene/ethanol, 9.5:0.5. Yield: 43%; m.p. 149-151° C. (ethyl acetate). IR ($CHCl_3$, $cm^{-1}$): 3400, 1770, 1718, 1610, 1558, 1488. $^1$H-NMR ($CDCl_3$, δ): 1.48-1.86 (m, 5H), 2.01-2.10 (m, 1H), 2.59-3.18 (m, 9H), 3.53 (t, J=7.0 Hz, 2H), 3.95-4.27 (m, 1H), 4.49 (dd, 1H, J=12.0; 6.0 Hz), 5.08 (s, 1H), 6.56-6.92 (m, 2H), 7.03-7.13 (m, 2H) $^{13}$C-NMR ($CDCl_3$, δ): 23.9; 24.4; 25.5; 25.9; 32.7; 39.1; 48.4; 54.0; 58.3; 63.2; 74.8; 116.7; 120.0; 122.0; 127.1; 129.4; 154.6; 159.6; 171.6. Analysis calculated for $C_{19}H_{24}N_3O_3S.HCl$: C, 55.40; H, 6.36; N, 10.20, found: C, 55.38; H, 6.44; N, 9.87.

Example 3

(±)-2-[4-[(Chroman-2-yl)methylamine]butyl]-1,3-dioxoperhydroimidazo[1,5-c]-thiazol, 3

Chromatography: toluene/ethanol, 9.5:0.5. Yield: 38%; m.p. 142-144° C. (ethyl acetate). IR ($CHCl_3$, $cm^{-1}$): 3400, 3500, 1770, 1716, 1582, 1540, 1508. $^1$H-NMR ($CDCl_3$, δ): 1.49-1.74 (m, 5H), 1.98-2.05 (m, 1H), 2.60-2.84 (m, 6H), 3.12 (dd, J=11.7; 5.8 Hz, 1H), 3.33 (dd, J=13.5; 8.5 Hz, 1H), 3.52 (t, J=7.0 Hz, 2H), 4.12 (d, J=9.9 Hz, 1H), 4.22-4.28 (m, 1H), 4.33 (dd, J=8.5; 5.8 Hz, 1H), 5.01 (d, J=9.9 Hz, 1H), 6.77-6.88 (m, 2H), 7.04-7.13 (m, 2H). $^{13}$C-NMR ($CDCl_3$, δ): 23.8; 24.4; 25.6; 25.9; 32.7; 39.1; 49.2; 54.1; 58.2; 64.4; 74.2; 116.7; 120.3; 122.0; 127.1; 129.5; 154.5; 159.6; 171.9. Analysis calculated for $C_{19}H_{24}N_3O_3S.HCl$: C, 55.40; H, 6.36; N, 10.20, found: C, 55.02; H, 6.44; N, 9.85.

Example 4

(±)-3-[4-[(Chroman-2-yl)methylamine]butyl]-2,4-dioxothiazolidin, 4

Chromatography: toluene/ethanol, 9.5:0.5. Yield: 45%; m.p. 126-127° C. (ethyl acetate). IR ($CHCl_3$, $cm^{-1}$): 3400, 1750, 1683, 1608, 1558, 1508. $^1$H-NMR ($CDCl_3$, δ): 1.47-1.76 (m, 5H), 2.01-2.06 (m, 1H), 2.57-3.01 (m, 6H), 3.62 (t, J=7.2 Hz, 2H), 3.92 (s, 2H), 4.10-4.25 (m, 1H), 6.74-6.83 (m, 2H), 7.01-7.08 (m, 2H). $^{13}$C-NMR ($CDCl_3$, δ): 24.2; 24.5; 25.3; 25.9; 33.7; 41.8; 54.2; 58.4; 74.3; 116.7; 120.0; 122.0; 127.1; 129.5; 154.5; 171.4; 171.8. Analysis calculated for $C_{17}H_{21}N_2O_3S.HCl$: C, 55.05; H, 6.25; N, 7.55, found: C, 54.98; H, 6.33; N, 7.15.

Example 5

(±)-3-[5-[(Chroman-2-yl)methylamine]pentyl]-2,4-dioxothiazolidin, 5

Chromatography: toluene/ethanol, 20:1→8:2. Yield: 38%; m.p. 172-174° C. (chloroform/ethyl acetate). IR ($CHCl_3$, $cm^{-1}$): 1751, 1682, 1683, 1608, 1581, 1488, 1456. $^1$H-NMR ($CDCl_3$, δ): 1.25-2.04 (m, 8H), 2.67 (t, J=7.0 Hz, 2H), 2.75-2.94 (m, 4H), 3.63 (t, J=7.3 Hz, 2H), 3.92 (s, 2H), 4.08-4.17 (m, 1H), 6.78-6.85 (m, 2H), 7.01-7.11 (m, 2H). $^{13}$C-NMR ($CDCl_3$, δ): 24.4; 24.6; 25.7; 27.4; 29.4; 33.7; 42.0; 49.6; 54.2; 75.0; 116.7; 120.2; 122.0; 127.2; 129.5; 154.6; 171.4; 171.7. Analysis calculated for $C_{18}H_{24}N_2O_3S.HCl$: C, 56.17; H, 6.55; N, 7.28, found: C, 55.49; H, 6.49; N, 7.10.

Example 6

(±)-3-[6-[(Chroman-2-yl)methylamine]hexyl]-2,4-dioxothiazolidin, 6

Chromatography: toluene/ethanol, 20:1. Yield: 30%; m.p. 175-177° C. (chloroform/ethyl acetate). IR ($CHCl_3$, $cm^{-1}$): 3416, 3321, 1751, 1670, 1608, 1581, 1489, 1456. $^1$H-NMR ($CDCl_3$, δ): 1.25-2.01 (m, 10H), 2.66 (t, J=7.1 Hz, 2H), 2.76-2.95 (m, 4H), 3.62 (t, J=7.3 Hz, 2H), 3.93 (s, 2H), 4.09-4.19 (m, 1H), 6.78-6.85 (m, 2H), 7.01-7.11 (m, 2H). $^{13}$C-NMR ($CDCl_3$, δ): 24.6; 25.7; 26.6; 26.8; 27.5; 29.8; 33.7; 42.0; 49.8; 54.2; 75.1; 116.7; 120.2; 122.0; 127.2; 129.5; 154.6; 171.4; 171.7. Analysis calculated for $C_{19}H_{26}N_2O_3S.HCl$: C, 57.18; H, 6.82; N, 7.02, found: C, 56.78; H, 6.72; N, 6.94.

Example 7

2-[4-[(Naphth-1-yl)methylamine]butyl]-1,3-dioxoperhydropyrrolo[1,2-c]imidazol, 7

Chromatography: ethyl acetate. Yield. 42%; m.p. 150-153° C. (chloroform/hexane). IR (CHCl$_3$, cm$^{-1}$): 3300-3500, 1770, 1708, 1696, 1510, 1442, 1416. $^1$H-NMR (CDCl$_3$, δ): 1.48-1.71 (m, 5H), 1.99-2.08 (m, 2H), 2.16-2.24 (m, 1H), 2.74 (t, J=6.9 Hz, 2H), 3.16-3.24 (m, 1H), 3.47 (t, J=6.9 Hz, 2H), 3.64 (dt, J=11.1; 7.8 Hz, 1H), 4.02 (dd, J=9.3; 7.8 Hz, 1H), 4.20 (s, 2H), 7.37-7.54 (m, 4H), 7.74 (d, J=7.2 Hz, 1H), 7.82-7.85 (m, 1H), 8.08 (d, J=8.4 Hz, 1H). $^{13}$C-NMR (CDCl$_3$, δ): 25.9; 27.0; 27.2; 27.5; 38.8; 45.5; 49.3; 51.6; 63.3; 123.6; 125.4; 125.6; 125.9; 126.1; 127.7; 128.7; 131.8; 133.9; 136.0; 160.9; 173.9. Analysis calculated for C$_{21}$H$_{25}$N$_3$O$_2$.HCl: C, 65.02; H, 6.76; N, 10.83, found: C, 64.53; H, 6.71; N, 10.44.

Example 8

2-[4-[(Naphth-2-yl)methylamine]butyl]-1,3-dioxoperhydropyrrolo[1,2-c]imidazol, 8

Chromatography: chloroform/methanol, 9:1. Yield: 25%; m.p. 125-127° C. (ethyl acetate). IR (CHCl$_3$, cm$^{-1}$): 3417, 1769, 1707. $^1$H-NMR (CDCl$_3$, δ): 1.52-1.80, 1.92-2.23 (m, 3H), 2.80 (t, J=7.1 Hz, 2H), 3.13-3.25 (m, 1H), 3.42 (t, J=6.6 Hz, 2H), 3.56-3.74 (m, 1H), 4.06-4.13 (m, 3H), 5.19 (sa, 1H), 7.45-7.50 (m, 2H), 7.61 (d, J=8.8 Hz, 1H), 7.78-7.92 (m, 4H). $^{13}$C-NMR (CDCl$_3$, δ): 25.2; 26.8; 27.3; 29.5; 37.8; 45.3; 46.2; 51.5; 63.2; 126.3; 126.4; 126.7; 127.5; 127.8; 128.6; 129.0; 130.0; 132.9; 133.0; 160.5; 173.8. Analysis calculated for C$_{21}$H$_{25}$N$_3$O$_2$.HCl.H$_2$O: C, 62.14; H, 6.95; N, 10.35. found: C, 62.54; H, 7.06; N, 9.95.

Example 9

2-[4-[2-(Naphth-1-yl)ethylamine]butyl]-1,3-dioxoperhydropyrrolo[1,2-c]imidazol, 9

Chromatography: ethyl acetate/ethanol, 1:1. Yield: 48%; m.p. 95-97° C. (ethyl acetate). IR (CHCl$_3$, cm$^{-1}$): 3400 (NHR, 1770, 1710. $^1$H-NMR (CDCl$_3$, δ): 1.56-1.78 (m, 5H), 2.00-2.28 (m, 3H), 2.72 (t, J=6.8 Hz, 2H), 3.02 (t, J=7.1 Hz, 2H), 3.11-3.38 (m, 3H), 3.48 (t, J=7.2 Hz, 2H), 3.63-3.74 (m, 1H), 4.01-4.10 (m, 1H), 7.37-7.54 (m, 4H), 7.71-7.76 (m, 1H), 7.82-7.86 (m, 1H), 7.08-7.13 (m, 1H). $^{13}$C-NMR (CDCl$_3$, δ): 27.9; 27.0; 27.1; 27.6; 33.4; 37.8; 45.5; 49.3; 50.4; 63.3; 123.7; 125.5; 125.9; 126.6; 127.0; 128.8; 132.0; 134.0; 136.0; 160.8; 174.0. Analysis calculated for C$_{22}$H$_{27}$N$_3$O$_2$.HCl.H$_2$O: C, 62.92; H, 7.20; N, 10.01, found: C, 63.40; H, 7.09; N, 9.61.

Example 10

3-[4-[2-(Naphth-1-yl)ethylamine]butyl]-2,4-dioxothiazolidin, 10

Chromatography: ethyl acetate. Yield: 37%; m.p. 128-129° C. (ethyl acetate). IR (CHCl$_3$, cm$^{-1}$): 1751, 1682, 1682, 1510. $^1$H-NMR (CDCl$_3$, δ): 1.52-1.63 (m, 4H), 2.70 (t, J=6.8 Hz, 2H), 2.94 (s, 1H), 3.03 (t, J=7.3 Hz, 2H), 3.32 (t, J=7.6 Hz, 2H), 3.62 (t, J=6.8 Hz, 2H), 3.93 (s, 2H), 7.33-7.55 (m, 4H), 7.71-7.75 (m, 1H), 7.83-7.88 (m, 1H), 8.04-8.08 (m, 1H). $^{13}$C-NMR (CDCl$_3$, δ): 25.4; 26.3; 32.7; 33.8; 41.7; 48.7; 49.9; 123.7; 125.7; 125.8; 126.1; 126.8; 127.3; 128.9; 131.0; 134.0; 135.4; 171.0; 171.5. Analysts calculated for C$_{19}$H$_{22}$N$_2$O$_2$S.HCl: C, 60.82; H, 6.85; N, 7.09, found: C, 62.87; H, 6.45; N, 6.90.

Example 11

2-[4-[2-(Naphth-2-yl)ethylamine]butyl]-1,3-dioxoperhydropyrrolo[1,2-c]imidazol, 11

Chromatography: ethyl acetate/ethanol, 9:1. Yield: 25%; m.p. 130-132° C. (ethyl acetate). IR (CHCl$_3$, cm$^{-1}$): 3421, 1769, 1705. $^1$H-NMR (CDCl$_3$, δ): 1.59-1.89 (m, 5H), 2.03-2.27 (m, 3H), 2.98 (t, J=7.8 Hz, 2H), 3.01-3.32 (m, 5H), 3.47 (t, J=6.6 Hz, 2H), 3.57-3.77 (m, 1H), 4.05 (dd, J=9.3; 7.3 Hz, 1H), 6.29 (sa, 1H), 7.32-7.48 (m, 3H), 7.68-7.80 (m, 4H). $^{13}$C-NMR (CDCl$_3$, δ): 25.4; 27.1; 27.5; 31.2; 33.1; 37.9; 45.5; 47.1; 49.1; 63.4; 125.5; 125.8; 126.2; 126.9; 127.4; 127.6; 128.6; 131.8; 133.5; 139.5; 160.7; 174.1. Analysis calculated for C$_{22}$H$_{27}$N$_3$O$_2$.HCl.H$_2$O: C, 62.92; H, 7.20; N, 10.01, found: C, 63.34; H, 7.46; N, 9.65.

Example 12

2-[4-[2-(Phenoxy)ethylamine]butyl]-1,3-dioxoperhydropyrrolo[1,2-c]imidazol, 12

Chromatography: toluene/ethanol, 9.5:0.5. Yield: 54%. m.p. 145-147° C. (ethyl acetate). IR (CHCl$_3$, cm$^{-1}$): 3315, 1770, 1709, 1599, 1587, 1497. $^1$H-NMR (CDC$_3$, δ): 1.47-1.77 (m, 6H), 1.98-2.29 (m, 3H), 2.70 (t, J=6.8 Hz, 2H), 2.99 (t, J=4.9 Hz, 2H), 3.23 (ddd, J=11.2; 7.6; 5.2 Hz, 1H), 3.49 (t, J=7.3 Hz, 2H), 3.67 (dt, J=11.2; 7.6 Hz, 1H), 4.02-4.10 (m, 3H), 6.87-6.98 (m, 3H), 7.23-7.32 (m, 2H). $^{13}$C-NMR (CDCl$_3$, δ): 26.0; 27.1; 27.3; 27.7; 38.9; 45.7; 48.9; 49.4; 63.4; 67.3; 114.7; 121.0; 129.6; 158.3; 160.7; 174.0. Analysis calculated for C$_{18}$H$_{25}$N$_3$O$_3$.HCl: C, 58.77; H, 7.12; N, 11.42, found: C, 58.79; H, 7.04; N, 11.16.

Example 13

3-[4-[2-(Phenoxy)ethylamine]butyl]-2,4-dioxothiazolidin, 13

Chromatography: ethyl acetate→ethyl acetate/ethanol, 9:1. Yield: 37%; m.p. 173-174° C. (ethyl acetate). IR (CHCl$_3$, cm$^{-1}$): 3413, 3327, 1751, 1685, 1599, 1587, 1497. $^1$H-NMR (CDCl$_3$, δ): 1.48-1.72 (m, 4H), 2.70 (t, J=7.1 Hz, 2H), 2.99 (t, J=7.9 Hz, 2H), 3.65 (t, J=7.1 Hz, 2H), 3.93 (s, 2H), 4.06 (t, J=5.1 Hz, 2H), 6.88-6.98 (m, 3H), 7.23-7.32 (m, 2H). $^{13}$C-NMR (CDC$_3$, δ): 25.4; 27.1; 33.7; 41.8; 48.8; 49.1; 67.1; 114.5; 120.8; 129.4; 158.8; 171.4; 171.5. Analysis calculated for C$_{15}$H$_{20}$N$_2$O$_3$S.HCl: C, 52.17; H, 6.14; N, 8.12, found: C, 51.77; H, 6.04; N, 8.10.

Example 14

2-[4-[2-(Naphth-1-oxi)ethylamine]butyl]-1,3-dioxoperhydropyrrolo[1,2-c]imidazol, 14

Chromatography: ethyl acetate→ethyl acetate/ethanol, 9:1. Yield: 43%; m.p. 163-164° C. (ethyl acetate). IR (CHCl$_3$, cm$^{-1}$): 3354, 1771, 1707, 1582, 1508. $^1$H-NMR (CDCl$_3$, δ): 1.58-1.77 (m, 5H), 1.93-2.30 (m, 3H), 2.86 (t, J=7.1 Hz, 2H), 3.15-3.27 (m, 3H), 3.49 (t, J=6.8 Hz, 2H), 3.60-3.73 (m, 1H), 4.05 (dd, J=9.0; 7.3 Hz, 1H), 4.30 (t, J=4.9 Hz, 2H), 6.80 (dd, J=8.5; 1.2 Hz, 1H), 7.31-7.53 (m, 4H), 7.75-7.83 (m, 1H), 8.22-8.28 (m, 1H). $^{13}$C-NMR (CDCl$_3$, δ): 25.7; 26.3; 27.0; 27.5; 38.5; 45.5; 48.3; 48.8; 63.3; 66.7; 104.9; 120.6; 121.9; 125.3; 125.8; 126.4; 127.5; 125.5; 134.5; 154.3; 160.8; 174.0. Analysis calculated for C$_{22}$H$_{27}$N$_3$O$_3$.HCl.H$_2$O: C, 60.61; H, 6.94; N, 9.64, found: C, 61.00; H, 6.57; N, 9.46.

Example 15

3-[4-[2-(Naphth-1-oxi)ethylamine]butyl]-2,4-dioxothiazolidin, 15

Chromatography: ethyl acetate→ethyl acetate/ethanol, 9:1. Yield: 46%; m.p. 149-151° C. (ethyl acetate). IR (CHCl$_3$, cm$^{-1}$): 3332, 1684, 1582, 1508. $^1$H-NMR (CDCl$_3$, δ): 1.58-1.70 (m, 4H), 2.81 (t, J=6.8 Hz, 2H), 3.17 (t, J=5.4 Hz, 2H), 3.65 (t, J=6.8 Hz, 2H), 3.92 (s, 2H), 4.27 (t, J=5.1 Hz, 2H), 6.81 (dd, J=7.1; 1.5 Hz, 1H), 7.30-7.56 (m, 4H), 7.75-7.83 (m, 1H), 8.22-8.38 (m, 1H). $^{13}$C-NMR (CDCl$_3$, δ): 25.3; 26.7; 33.7; 41.7; 48.5; 48.9; 67.1; 104.9; 120.5; 121.9; 125.2; 125.8; 126.4; 127.5; 125.6; 134.5; 154.4; 171.4; 171.5. Analysis calculated for C$_{19}$H$_{22}$N$_2$O$_3$S.HCl: C, 57.79; H, 5.87; N, 7.09, found: C, 57.75; H, 5.79; N, 6.59.

Example 16

2-[4-[(Benzimidazol-2-yl)methylamine]butyl]-1,3-dioxoperhydropyrrolo[1,2-c]imidazol, 16

Chromatography: toluene/ethanol, 9.5:0.5. Yield: 50%; m.p. 208-210° C. (ethyl acetate). IR (CHCl$_3$, cm$^{-1}$): 3400, 1775, 1714. $^1$H-NMR (CDCl$_3$, δ): 1.42-1.70 (m, 5H), 1.92-2.28 (m, 3H), 2.63 (t, J=6.5 Hz, 2H), 3.13-3.25 (m, 1H), 3.43 (t, J=6.5 Hz, 2H), 3.55-3.64 (m, 1H), 4.00 (m, 2H), 7.10-7.18 (m, 2H), 7.47-7.53 (m, 2H). $^{13}$C-NMR (CDCl$_3$, δ): 25.4; 26.2; 27.0; 27.5; 38.4; 45.4; 47.6; 48.5; 63.3; 115.0; 122.0; 139.0; 154.0; 160.8; 174.0.

Example 17

2-[4-[(o-Methoxyphenyl)methylamine]butyl]-1,3-dioxoperhydropyrrolo[1,2-c]imidazol, 17

Chromatography: ethyl acetate/hexane. Yield: 42%; oil. IR (CHCl$_3$, cm$^{-1}$): 3016-2837, 1770, 1706, 1600, 1492, 1442, 1415, 1242. $^1$H-NMR (CDCl$_3$, δ): 1.47-1.72 (m, 3H), 1.95-2.09 (m, 2H), 2.17-2.28 (m, 1H), 2.59 (t, J=7.1 Hz, 2H), 3.18-3.26 (m, 1H), 3.45 (t, J=7.1 Hz, 2H), 3.65 (dt, J=11.1; 7.9 Hz, 1H), 3.76 (s, 2H), 3.82 (s, 3H), 4.04 (dd, J=9.3; 7.9 Hz, 1H), 6.83-6.91 (m, 2H), 7.20-7.25 (m, 2H). $^{13}$C-NMR (CDCl$_3$, δ): 24.4; 26.0; 27.0; 27.5; 38.9; 45.5; 47.1; 53.3; 63.3; 110.1; 120.3; 127.1; 130.3; 157.5; 160.9; 174.0. Analysis calculated for C$_{18}$H$_{24}$N$_3$O$_3$.HCl.3/2.H$_2$O: C, 54.88; H, 7.16; N, 10.67, found: C, 54.52; H, 7.09; N, 10.52.

Example 18

2-[4-[2-(o-Methoxyphenyl)ethylamine]butyl]-1,3-dioxoperhydropyrrolo[1,2-c]imidazol, 18

Chromatography: ethyl acetate/hexane. Yield. 25%; m.p. 160-162° C. (chloroform/hexane). IR (CHCl$_3$, cm$^{-1}$): 3018-2899, 1770, 1709, 1495, 1443, 1418, 1244. $^1$H-NMR (CDCl$_3$, δ): 1.60-1.77 (m, 5H), 1.96-2.27 (m, 3H), 2.75 (t, J=6.8 Hz, 2H), 2.92 (s, 4H), 3.15-3.27 (m, 1H), 3.45 (t, J=6.6 Hz, 2H), 3.65 (dt, J=11.0; 7.6 Hz, 1H), 3.79 (s, 3H), 4.05 (dd, J=9.0; 7.3 Hz, 1H), 4.62 (sa, 1H), 6.80-6.89 (m, 2H), 7.13-7.22 (m, 2H). $^{13}$C-NMR (CDCl$_3$, δ): 25.6; 27.0; 27.5; 27.5; 29.7; 38.4; 45.5; 48.3; 48.7; 55.2; 63.3; 110.3; 120.5; 127.2; 127.7; 130.4; 157.5; 160.7; 173.9. Analysis calculated for C$_{19}$H$_{26}$N$_3$O$_3$.HCl.H$_2$O: C, 57.20; H, 7.33; N, 10.53, found: C, 57.43; H, 7.03; N, 10.41.

Example 19

2-[4-[3-(o-Methoxyphenyl)propylamine]butyl]-1,3-dioxoperhydropyrrolo[1,2-c]imidazol, 19

Chromatography: toluene/methanol. Yield: 52%; oil. IR (CHCl$_3$, cm$^{-1}$): 3018-2700, 1772, 1709, 1492, 1442, 1418, 1244. $^1$H-NMR (CDCl$_3$, δ): 1.60-1.81 (m, 5H), 1.93-2.34 (m, 5H), 2.67 (t, J=6.8 Hz, 2H), 2.77 (m, 4H), 3.16-3.28 (m, 1H), 3.46 (t, J=6.6 Hz), 3.67 (dt, J=11.1; 7.6 Hz, 1H), 3.75 (s, 3H), 4.07 (dd, J=9.3; 7.3 Hz, 1H), 6.81-6.90 (m, 2H), 7.10-7.21 (m, 2H). $^{13}$C-NMR (CDCl$_3$, δ): 24.9; 25.6; 27.1; 27.5; 27.6; 27.9; 38.3; 45.6; 48.1; 48.4; 55.4; 63.4; 110.4; 120.6; 127.4; 129.3; 130.0; 157.4; 160.8; 174.0. Analysis calculated for C$_{20}$H$_{28}$N$_3$O$_3$.HCl.3/2H$_2$O: C, 56.93; H, 7.64; N, 9.93, found: C, 57.23; H, 7.21; N, 9.40.

Example 20

2-[4-[4-(o-Methoxyphenyl)butylamine]butyl]-1,3-dioxoperhydropyrrolo[1,2-c]imidazol, 20

Chromatography: chloroform/methanol, 9.5:0.5. Yield: 27% (oil). IR (CHC$_3$, cm$^{-1}$): 3700, 1770, 1709, 1601, 1443, 1495, 1585, 1215. $^1$H-NMR (CDCl$_3$, δ): 1.58-1.74 (m, 9H), 2.01-2.11 (m, 2H), 2.17-2.27 (m, 1H), 2.60 (t, J=7.3 Hz, 2H), 2.65-2.570 (m, 4H), 3.18-3.26 (m, 1H), 3.46 (t, J=6.8 Hz, 2H), 3.66 (dt, J=11.2; 7.6 Hz, 1H), 3.79 (s, 3H), 4.05 (dd, J=9.0; 7.6 Hz, 1H), 6.80-6.87 (m, 2H), 7.09-7.17 (m, 2H). $^{13}$C-NMR (CDCl$_3$, δ): 23.4; 25.2; 26.3; 27.0; 27.4; 29.6; 37.8; 45.4; 47.1; 47.8; 55.1; 63.4; 110.1; 120.3; 127.1; 129.7; 129.9; 157.2; 160.6; 173.9. Analysis calculated for C$_{21}$H$_3$N$_3$O$_3$.HCl.3/2H$_2$O: C, 60.31; H, 7.95; N, 10.05, found: C, 60.70; H, 7.56; N, 9.77.

Example 21

2-[3-[3-(o-Methoxyphenyl)propylamine]propyl]-1,3-dioxoperhydropyrrolo[1,2-c]imidazol, 21

Chromatography: chloroform/methanol, 9.5:0.5. Yield: 27% (oil). IR (CHCl$_3$, cm$^{-1}$): 3700, 1770, 1707, 1601, 1587, 1493, 1445, 1215. $^1$H-NMR (CDCl$_3$, δ): 1.62-1.86 (m, 5H), 2.02-2.32 (m, 3H), 2.56-2.67 (m, 6H), 3.24 (m, 1H), 3.54 (t, J=6.8 Hz, 2H), 3.67 (dt, J=11.2; 7.6 Hz, 1H), 3.81 (s, 3H), 4.06 (dd, J=9.0; 7.3 Hz, 1H), 6.81-6.91 (m, 2H), 7.10-7.22 (m, 2H). $^{13}$C-NMR (CDCl$_3$, δ): 26.9; 27.5; 27.8; 28.4; 30.0; 36.9; 45.5; 46.7; 49.5; 55.2; 63.3; 110.2; 120.3; 127.0; 129.8; 130.5; 157.4; 160.9; 174.0. Analysis calculated for C$_{18}$H$_{25}$N$_3$O$_3$.HCl.3H$_2$O: C, 51.24; H, 7.64; N, 9.96, found: C, 51.26; H, 7.25; N, 9.57.

Example 22

Determination of the Receptor Affinity

Biochemical studies to determine the affinity of synthesized compounds have been carried out by radioligand displacement experiments, experiments being carried out to determine the receptor affinity for the 5-HT$_{1A}$, 5-HT$_{2A}$, 5-HT$_3$, 5-HT$_4$, 5-HT$_7$, α$_1$ and D$_2$ receptors.

The conditions for each receptor studied is summarized in Table 1 below, while the receptor affinity data is summarized in Table 2 below.

TABLE 1

Conditions used for determination of receptor affinity.

| Receptor | Radioligand | Tissue | Unspecific bond | Medium | Temperature | Time |
|---|---|---|---|---|---|---|
| 5-HT$_{1A}$ | [$^3$H]-8-OH-DPAT | Rat cerebral cortex | 5-HT 10 μM | 1 | 37° C. | 15 min |
| 5-HT$_{2A}$ | [$^3$H]Ketanserine | Rat cerebral cortex | Cinanserine 1 μM | 2 | 37° C. | 15 min |
| 5-HT$_3$ | [$^3$H]LY 278584 | Rat cerebral cortex | 5-HT 10 μM | 3 | 25° C. | 30 min |
| 5-HT$_4$ | [$^3$H]GR 113808 | Rat striatum | 5-HT 30 μM | 4 | 37° C. | 30 min |
| 5-HT$_7$ | [$^3$H]-5-CT | Rat hypothalamus | 5-HT 10 μM | 5 | 23° C. | 120 min |
| α$_1$ | [$^3$H]prazosin | Rat cerebral cortex | Phentolamine 10 μM | 6 | 25° C. | 30 min |
| D$_2$ | [$^3$H]spiperone | Rat striatum | (±)Butaclamol 1 μM | 7 | 37° C. | 15 min |

Incubation medium:

1. MgSO$_4$ 5 mM and EDTA 0.5 mM in Tris-HCl 50 mM, pH 7.4
2. MgSO$_4$ 10 mM, EDTA 0.5 mM, ascorbic acid 0.1% and pargiline 10 μM in Tris-HCl 50 mM, pH 7.4
3. Pargiline 10 μM, ascorbic acid 0.6 mM and CaCl$_2$ 5 mM in Tris-HCl 50 mM, pH 7.4
4. HEPES 50 mM, pH 7.4
5. CaCl$_2$ 4 mM, ascorbic acid 1 mg/mL, pargiline 0.01 mM and (−)pindolol 3 μM in Tris-HCl 50 mM, pH 7.4
6. MgCl$_2$ 2.5 mM in Tris-HCl 50 mM, pH 7.4
7. NaCl 120 mM, KCl 5 mM, CaCl$_2$ 1 mM and ascorbic acid 5.7 mM in Tris-HCl 50 mM, pH 7.4

TABLE 2

Receptor affinity data obtained.

| Compound | $K_i$ ± E.E. (nM) | | | | | | |
|---|---|---|---|---|---|---|---|
| | 5-HT$_{1A}$ | 5-HT$_{2A}$ | 5-HT$_3$ | 5-HT$_4$ | 5-HT$_7$ | α$_1$ | D$_2$ |
| 1 | 1.23 ± 0.09 | >10000 | >10000 | >10000 | 299.3 ± 7.7 | 121.1 ± 1.8 | >1000 |
| 2 | 19.9 ± 6.0 | >1000 | >10000 | >10000 | 492.7 ± 1.5 | 50.0 ± 6.2 | >10000 |
| 3 | 13.2 ± 1.0 | >1000 | >10000 | >10000 | >1000 | 8.5 ± 0.6 | >10000 |
| 4 | 30.1 ± 0.6 | >1000 | >10000 | >10000 | 168.8 ± 18.1 | >1000 | >10000 |
| 5 | 5.5 ± 0.4 | >1000 | >10000 | >10000 | 123.0 ± 17.8 | 27.7 ± 4.0 | >10000 |
| 6 | 1.3 ± 0.2 | >1000 | >10000 | >10000 | 87.0 ± 3.1 | 26.3 ± 2.4 | >10000 |
| 7 | >1000 | >1000 | NA | >10000 | >10000 | 49.6 ± 2.9 | >10000 |
| 8 | 51.01 ± 0.47 | >1000 | >10000 | NA | 8.04 ± 0.87 | >10000 | >10000 |
| 9 | 27.9 ± 3.1 | >10000 | >1000 | >10000 | >1000 | >1000 | >10000 |
| 10 | 15.0 ± 1.0 | >1000 | >1000 | >1000 | >10000 | >1000 | >10000 |
| 11 | 43.2 ± 4.5 | 157.3 ± 0.65 | >10000 | 594.3 ± 43.7 | 74.05 ± 7.3 | 99.05 ± 14 | NA |
| 12 | 25.5 ± 0.9 | >10000 | >1000 | >10000 | >1000 | >1000 | >1000 |
| 13 | 9.8 ± 0.7 | >10000 | >10000 | >1000 | 55.0 ± 0.3 | 26.9 ± 4.5 | >10000 |
| 14 | 2.4 ± 0.6 | 41.5 ± 7.5 | >1000 | >10000 | 42.6 ± 4.4 | 30.9 ± 4.9 | >1000 |
| 15 | 4.5 ± 0.2 | 38.5 ± 7.7 | >10000 | NA | 19.9 ± 0.8 | 54.7 ± 1.8 | >1000 |
| 16 | >10000 | >10000 | >1000 | >10000 | >10000 | >1000 | >10000 |
| 17 | >10000 | NA | NA | NA | NA | >10000 | NA |
| 18 | 868.5 ± 23.1 | >10000 | NA | >10000 | NA | >1000 | >10000 |
| 19 | 73.9 ± 5.0 | >1000 | >10000 | >10000 | >10000 | >1000 | >10000 |
| 20 | 137.6 ± 26.3 | >10000 | >1000 | >10000 | >10000 | >1000 | >10000 |
| 21 | >1000 | >10000 | >10000 | >1000 | >10000 | >1000 | >10000 |
| 5-HT | 0.84 ± 0.27 | 5.9 ± 0.2 | 13.8 ± 2.4 | 53.8 ± 3.3 | 4.2 ± 0.5 | — | — |
| 8-OH-DPAT | 1.0 ± 0.1 | — | — | — | 83.8 | — | — |
| Cinanserine | — | 2.6 ± 0.4 | — | — | — | — | — |
| Ondansetron | — | — | 0.77 ± 0.01 | — | — | — | — |
| RS-39604 | — | — | — | 3.9 ± 0.2 | — | — | — |
| 5-CT | — | — | — | — | 1.8 ± 0.6 | — | — |
| Phentolamine | — | — | — | — | — | 6.1 ± 0.1 | — |
| Butaclamol | — | — | — | — | — | — | 49.0 ± 5.8 |

Example 23

In Vitro Functional Characterization

The functional character of the new compounds was initially determined by studying their effect on adenylate cyclase in He—La cells transfected with the 5-human $HT_{1A}$ receptor, measuring their inhibiting effect on the stimulation of the enzyme induced by forskolin (Table 3 below). The compounds included in this table behaved in all cases as pure agonists, so as to reach values close to 100% of inhibition of the activation induced by forskolin. The 50 effective concentration ($CE_{50}$) a concentration that produces 50% of the inhibition of the increase in enzymatic activity by forskolin, was in the nanomolar range. The action of the new compounds in this test was mediated in by the $5\text{-}HT_{1A}$ receptor as can be deduced from the blocking of the effect of all compounds studied by the selective $5\text{-}HT_{1A}$ antagonist WAY-100635 ($10^{-8}$ M).

TABLE 3

Test on adenylate cyclase in He—La cells

| Compound no. | $CE_{50}$ (nM) | % Maximum inhibition |
|---|---|---|
| 1 | 16.3 | 94.6 |
| 2 | 18.9 | 94.5 |
| 3 | 31.5 | 89.3 |
| 4 | 11.6 | 89.6 |
| 12 | 76.2 | 87.4 |

The in vitro agonist character of the new compounds was also evaluated in some cases by the fixation test of $[^{35}S]$-GTPγS to coronal sections of rat brain. In this test, the results obtained with compounds no. 1 and no. 3, at a concentration of 10 μM, were especially similar to those obtained with the $5\text{-}HT_{1A}$, 8-OH-DPAT agonist prototype. In the autoradiograms, an increase in intensity of the signal in the hippocampus (CA1, CA2, CA3 and dentate gyrus), thalamic nuclei, amygdaloid complex, cortex and in the mediobasal hypothalamus nuclei was observed. The increase in intensity of the marking in these cerebral areas was reduced until reaching control levels when the incubation was carried out in the presence of both the molecule under study and the selective $5\text{-}HT_{1A}$ antagonist WAY-100635 (1 μM).

The five compounds included in Table 3 likewise produced hyperpolarization of the potential of the neurons of the hippocampal area CA1. By carrying out dose-effect curves, it was observed that the action of compounds no. 1 and no. 2 in this test was indistinguishable in potency to that of the $5\text{-}HT_{1A}$, 8-OH-DPAT type agonist.

Example 24

In Vivo Functional Characterization

All compounds previously characterized in vitro as $5\text{-}HT_{1A}$ agonists (Table 3) were delivered by subcutaneous injection to mice in order to quantify the hypothermia associated to stimulation of this serotonergic receptor subtype. In all cases, a reduction in the rectal temperature of the mouse was observed of a variable duration ranging from between 30 and 120 minutes. In Table 4 below, the minimum effective doses for each compound studied and the degree of hypothermia reached at this dose are shown. The maximum hypothermic effect was reached wish doses 4-8 times higher than those indicated in this Table 4, in some cases reaching temperature decreases of 4° C.

TABLE 4

Mouse hypothermia test

| Compound no. | Minimum effective dosage (mg/kg) | Hypothermic effect (° C.) |
|---|---|---|
| 1 | 2.5 | 1.4 |
| 2 | 1.25 | 1.5 |
| 3 | 1.25 | 1.3 |
| 4 | 0.3 | 2.0 |
| 12 | 2.5 | 1.4 |

Example 25

Determination of the In Vitro Neuroprotective Action

The neuroprotective effect of the compounds considered was studied in experimental models in vitro, using primary cultures of rat hippocampus exposed to serum deprivation, to a toxic concentration of glutamate, or incubated in conditions of hypoxia and absence of glucose.

In the model of apoptotic neuronal death induced by incubation of mixed cultures of neurons and glial cells for 24 hours in a medium without serum, the neuroprotective effect of compound no. 1 is to be highlighted, with which a concentration-dependent effect was observed which was even higher (more than 40% protection) than that obtained with the 8-OH-DPAT agonist. Other compounds were also shown to be effective such as no. 4 and no. 12, although in both cases the degree of protection was somewhat below at the various concentrations used in the tests.

In the model of excitotoxic neuronal death due to exposure of the neuronal cultures to 1 mM glutamate, compound 1 was that which most effectively prevented (37%) the associated damage. Likewise, this compound showed a neuroprotective effect (>20%) in the model of neuronal death due to exposure of the cultures to a transient hypoxia situation in the absence of glucose and subsequent incubation in a 5% $CO_2$ atmosphere.

Example 26

Determination of the In Vivo Neuroprotective Action

The in vivo neuroprotective action was evaluated both in the transient global ischemia model in gerbils and in the permanent focal ischemia model in rats.

In the transient ischemia model in gerbils induced by temporary occlusion of both carotid arteries, the delivery of compounds no. 1 and no. 12, 30 minutes before the induction of the ischemia, and 24 and 48 hours afterwards, significantly prevented the injury induced by the ischemic process in the hippocampal area CA1, which was evaluated by Nissl stain. The neuroprotective effect was dose-dependent, between 1-5 mg/kg by subcutaneous injection, reaching, with compound no. 1, a degree of total protection of the injury in approximately half the animals at a dose of 5 mg/kg. This protection was accompanied by a hypothermic effect, likewise dependent on the dose delivered.

In the focal ischemia model due to permanent occlusion of the middle cerebral artery in the rat, the delivery of compound no. 1 by intravenous injection, 45 minutes before and 45 minutes after the occlusion, significantly reduced the volume of the infarcted area. Specifically, at a dose of 2 mg/kg, the infarction volume was reduced by more than 25%.

The invention claimed is:

1. A compound, a stereochemical isomer of the compound, or a solvate or pharmaceutically acceptable salt of the compound or isomer, wherein the compound corresponds in structure to Formula I:

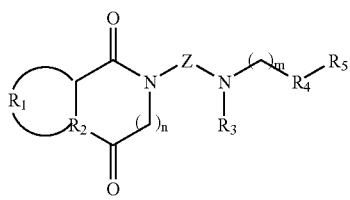

Formula I wherein:
  $R_2$ is selected from the group consisting of N, NH and S; wherein
    if $R_2$ is N, then $R_1$ is selected from the group consisting of —(CH$_2$)$_3$—,—(CH$_2$)$_4$—,—CH$_2$SCH$_2$, and —SCH$_2$CH$_2$—;
    if $R_2$ is S or NH, then $R_1$ is absent;
    if $R_2$ is NH, then n is 1;
  n has a value of zero or 1;
  Z is selected from the group consisting of $C_2$-$C_{10}$-alkyl, $C_2$-$C_{10}$-alkenyl, and $C_2$-$C_{10}$-alkynyl;
  $R_3$ is selected from the group consisting of H, $C_1$-$C_{10}$-alkyl, aryl, and aralkyl;
  m has a value of zero, 1, or 2;
  $R_4$ is selected from the group consisting of O and CH$_2$;
  $R_5$ is selected from the group consisting of

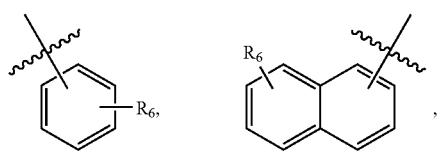

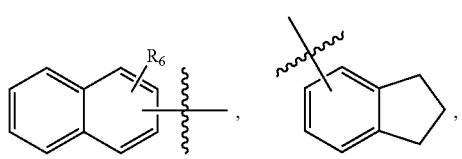

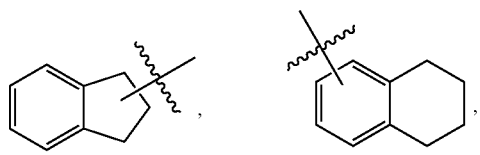

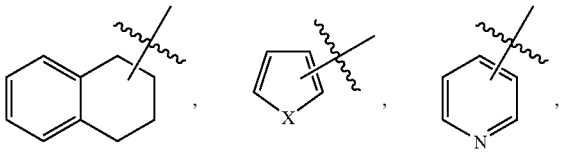

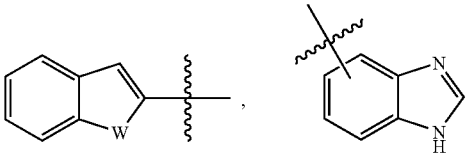

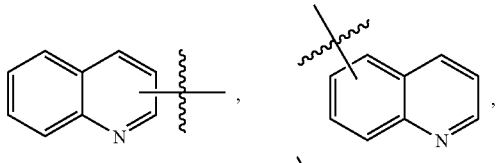

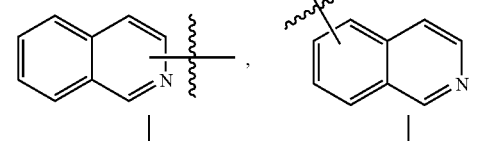

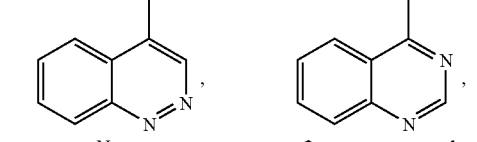

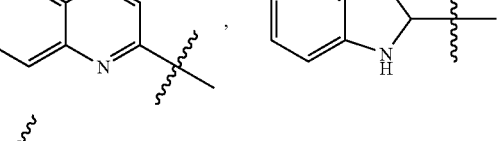

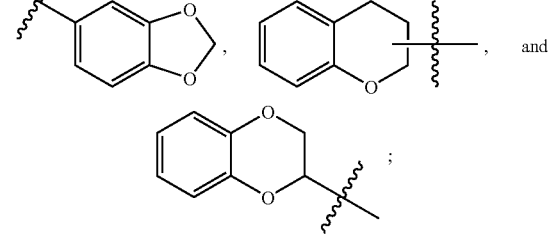

wherein:
  $R_6$ is selected from the group consisting of H, $C_1$-$C_5$-alkyl, $C_1$-$C_5$-alkoxyl, OH, F, Cl, Br, and I;
  X is selected from the group consisting of O, S, NH, and NCH$_3$;
  Y is selected from the group consisting of O and NH;
  W is selected from the group consisting of S and NH.

2. The compound, a stereochemical isomer of the compound, or a solvate or pharmaceutically acceptable salt of the compound or isomer according to claim 1, wherein:

Z is $C_2$-$C_{10}$-alkyl; and $R_5$ is selected from the group consisting of

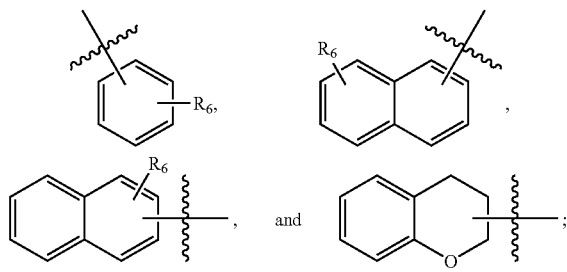

wherein:
  $R_6$ is selected from the group consisting of H, $C_1$-$C_5$-alkyl, $C_1$-$C_5$-alkoxyl, OH, F, Cl, Br, and I.

3. The compound, a stereochemical isomer of the compound, or a solvate or pharmaceutically acceptable salt of the compound or isomer according to claim 1, wherein:
  Z is butyl;
  $R_3$ is H; and
  $R_5$ is selected from the group consisting of

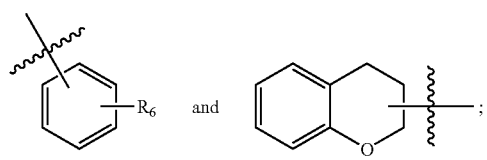

wherein:
  $R_6$ is selected from the group consisting of H $C_1$-$C_5$-alkyl, $C_1$-$C_5$-alkoxyl, OH, F, Cl, Br, and I.

4. A process to prepare a compound, a stereochemical isomer of the compound, or a solvate or pharmaceutically acceptable salt of the compound or isomer, wherein the compound corresponds in structure to Formula I:

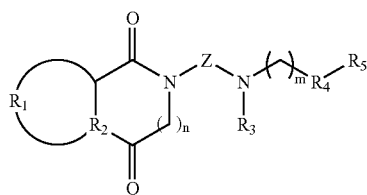

Formula I wherein:
  $R_2$ is selected from the group consisting of N, NH and S; wherein
    if $R_2$ is N, then $R_1$ is selected from the group consisting of —$(CH_2)_3$—, —$(CH_2)_4$—, —$CH_2SCH_2$, and —$SCH_2CH_2$—;
    if $R_2$ is S or NH, then $R_1$ is absent;
    if $R_2$ is NH, then n is 1;
  n has a value of zero or 1;
  Z is selected from the group consisting of $C_2$-$C_{10}$-alkyl, $C_2$-$C_{10}$-alkenyl, and $C_2$-$C_{10}$-alkynyl;
  $R_3$ is selected from the group consisting of H, $C_1$-$C_{10}$-alkyl, aryl, and aralkyl;
  m has a value of zero, 1, or 2;

$R_4$ is selected from the group consisting of O and $CH_2$;

$R_5$ is selected from the group consisting of

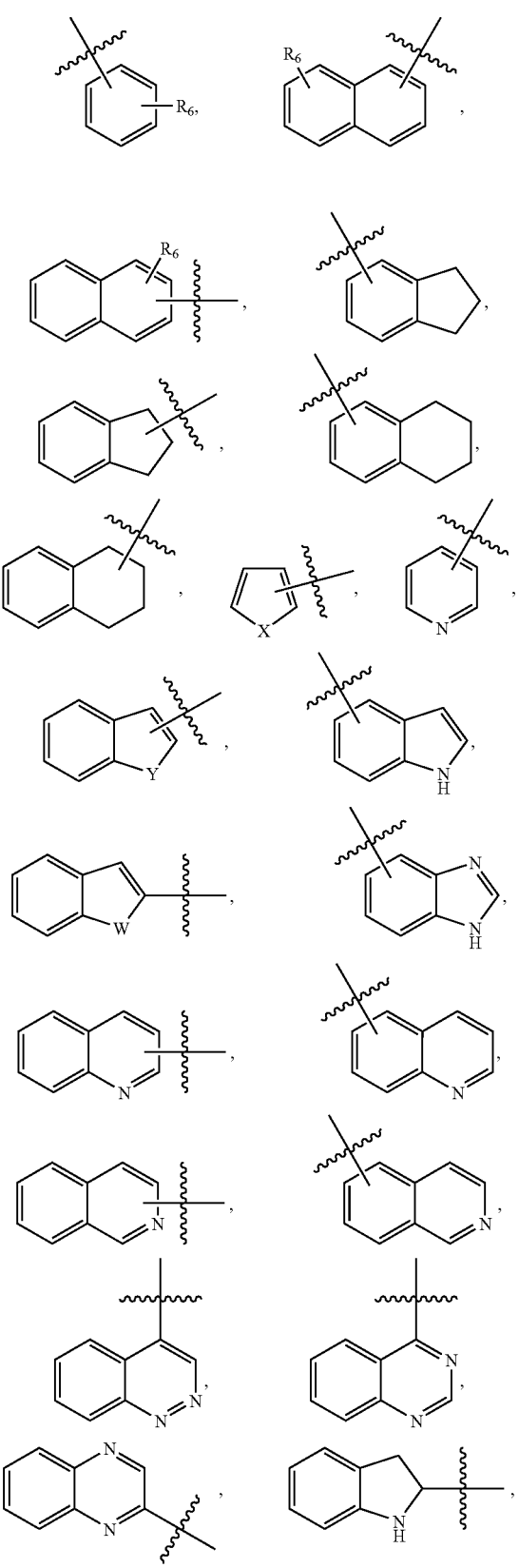

-continued

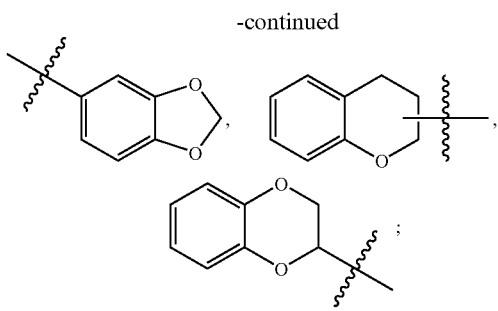

wherein:

$R_6$ is selected from the group consisting of H, $C_1$-$C_5$-alkyl, $C_1$-$C_5$-alkoxyl, OH, F, Cl, Br, and I;

X is selected from the group consisting of O, S, NH, and $NCH_3$;

Y is selected from the group consisting of O and NH; and

W is selected from the group consisting of S and NH comprising:

reacting compounds according to Formula II with compounds according to Formula III according to scheme I:

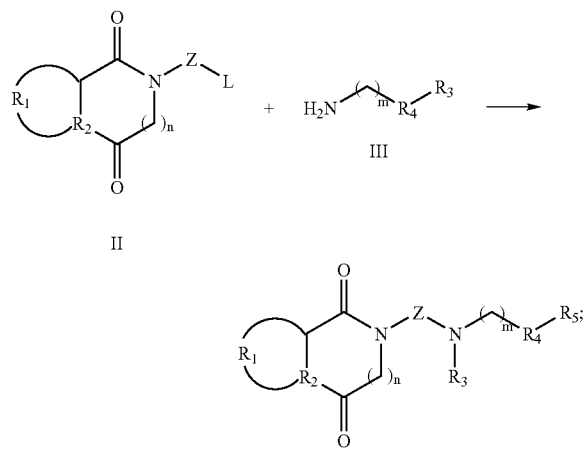

or reacting the compounds of Formula IV with the compounds of Formula V according to scheme II:

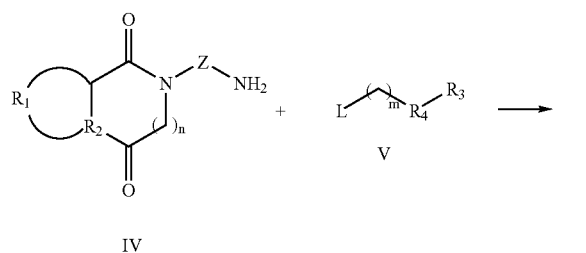

-continued

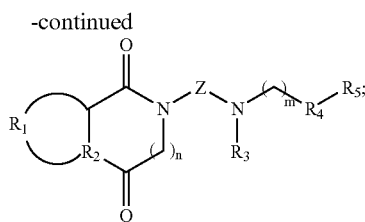

wherein:

L is selected from the group consisting of Cl and Br; and the definitions of $R_1$, $R_2$, n, Z, m, $R_4$ and $R_5$ are identical to those in Formula I.

5. A process according to claim 4, wherein compounds with $R_3$ selected from the group consisting of $C_1$-$C_{10}$-alkyl, aryl and aralkyl are obtained by alkylation of the analogues wherein $R_3$ is hydrogen.

6. A pharmaceutical composition comprising a therapeutically effective quantity of a compound, a stereochemical isomer of the compound, or a solvate or pharmaceutically acceptable salt of the compound or isomer, wherein the compound corresponds in structure to Formula I Formula I

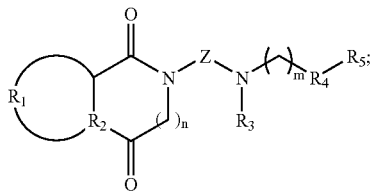

wherein:

$R_2$ is selected from the group consisting of N, NH and S; wherein
  if $R_2$ is N, then $R_1$ is selected from the group consisting of —$(CH_2)_3$—, —$(CH_2)_4$—, —$CH_2SCH_2$, and —$SCH_2CH_2$—;
  if $R_2$ is S or NH, then $R_1$ is absent;
  if $R_2$ is NH, then n is 1;

n has a value of zero or 1;

Z is selected from the group consisting of $C_2$-$C_{10}$-alkyl, $C_2$-$C_{10}$-alkenyl, and $C_2$-$C_{10}$-alkynyl;

$R_3$ is selected from the group consisting of H, $C_1$-$C_{10}$-alkyl, aryl, and aralkyl;

m has a value of zero, 1, or 2;

$R_4$ is selected from the group consisting of O and $CH_2$;

$R_5$ is selected from the group consisting of

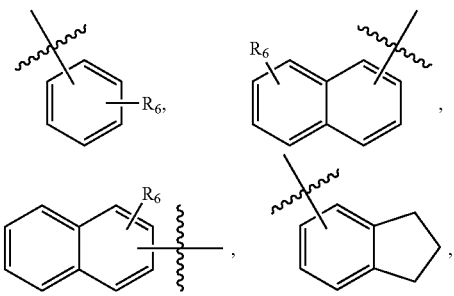

-continued

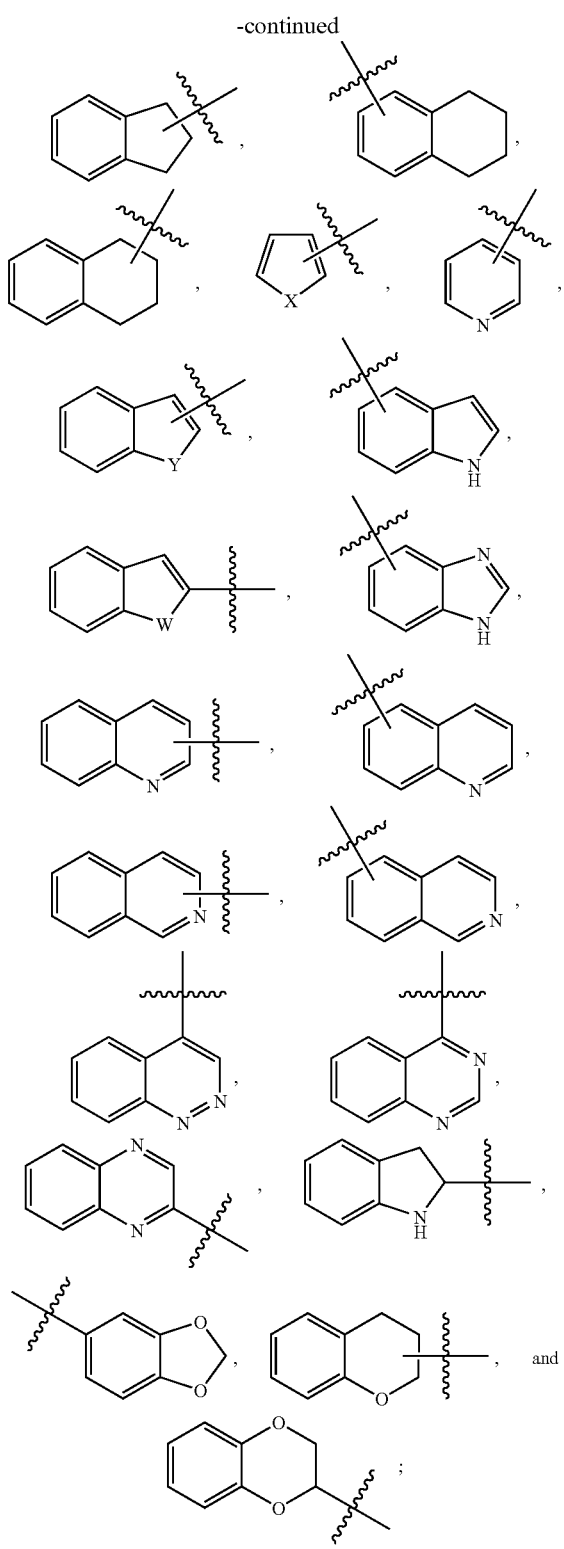

wherein:
R$_6$ is selected from the group consisting of H, C$_1$-C$_5$-alkyl, C$_1$-C$_5$-alkoxyl, OH, F, Cl, Br, and I;
X is selected from the group consisting of O, S, NH, and NCH$_3$;
Y is selected from the group consisting of O and NH;
W is selected from the group consisting of S and NH;
and one or more pharmaceutically acceptable carriers or excipients.

7. The compound, a stereochemical isomer of the compound, or a solvate or pharmaceutically acceptable salt of the compound or isomer according to claim 1 selected from the group consisting of
(±)2-[4-[(Chroman-2-yl)methylamine]butyl]-1,3-dioxoperhydropyrrolo[1,2-c]imidazol;
(±)-2-[4-[(Chroman-2-yl)methylamine]butyl]-1,3-dioxoperhydroimidazo[1,5-c]-thiazol;
(±)-2-[4-[(Chroman-2-yl)methylamine]butyl]-1,3-dioxoperhydroimidazo[1,5-c]-thiazol;
(±)-3-[4-[(Chroman-2-yl)methylamine]butyl]-2,4-dioxothiazolidin;
(±)-3-[5-[(Chroman-2-yl)methylamine]pentyl]-2,4-dioxothiazolidin;
(±)-3-[6-[(Chroman-2-yl)methylamine]hexyl]-2,4-dioxothiazolidin;
2-[4-[(Naphth-1-yl)methylamine]butyl]-1,3-dioxoperhydropyrrolo[1,2-c]imidazol;
2-[4-[(Naphth-2-yl)methylamine]butyl]-1,3-dioxoperhydropyrrolo[1,2-c]imidazol;
2-[4-[2-(Naphth-1-yl)ethylamine]butyl]-1,3-dioxoperhydropyrrolo[1,2-c]imidazol;
3-[4-[2-(Naphth-1-yl)ethylamine]butyl]-2,4-dioxothiazolidin;
2-[4-[2-(Naphth-2-yl)ethylamine]butyl]-1,3-dioxoperhydropyrrolo[1,2-c]imidazol;
2-[4-[2-(Phenoxy)ethylamine]butyl]-1,3-dioxoperhydropyrrolo[1,2-c]imidazol;
3-[4-[2-(Phenoxy)ethylamine]butyl]-2,4-dioxothiazolidin;
2-[4-[2-(Naphth-1-ethylamine]butyl]-1,3-dioxoperhydropyrrolo[1,2-c]imidazol;
3-[4-[2-(Naphth-1-ethylamine]butyl]-2,4-dioxothiazolidin;
2-[4-[(Benzimidazol-2-yl)methylamine]butyl]-1,3-dioxoperhydropyrrolo[1,2-c]imidazol;
2-[4-[(o-Methoxyphenyl)methylamine]butyl]-1,3-dioxoperhydropyrrolo[1,2-c]imidazol;
2-[4-[2-(o-Methoxyphenyl)ethylamine]butyl]-1,3-dioxoperhydropyrrolo[1,2-c]-imidazol;
2-[4-[3-(o-Methoxyphenyl)propylamine]butyl]-1,3-dioxoperhydropyrrolo[1,2-c]imidazol;
2-[4-[4-(o-Methoxyphenyl)butylamine]butyl]-1,3-dioxoperhydropyrrolo[1,2-c]imidazol; and
2-[3-[3-(o-Methoxypropylamine]propyl]-1,3-dioxoperhydropyrrolo[1,2-c]imidazol.

8. The compound, a stereochemical isomer of the compound, or a solvate or pharmaceutically acceptable salt of the compound or isomer according to claim 1 selected from the group consisting of
2-[4-[(chroman-2-yl)methylamino]butyl]-1,3-dioxoperhydropyrrolo[1,2-c]imidazole;
3-[4-[(chroman-2-yl)methylamino]butyl]-2,4-dioxothiazolidine;
3-[5-[(chroman-2-yl)methylamino]pentyl]-2,4-dioxothiazolidine;
3-[6-[(chroman-2-yl)methylamino]hexyl]-2,4-dioxothiazolidine;
2-[4-[2-(phenoxy)ethylamino]butyl]-1,3-dioxoperhydropyrrolo[1,2-c]imidazole; and
3-[4-[2-(phenoxy)ethylamino]butyl]-2,4-dioxothiazolidine.

9. The process of claim 4, wherein:
Z is $C_2$-$C_{10}$-alkyl; and
$R_5$ is selected from the group consisting of

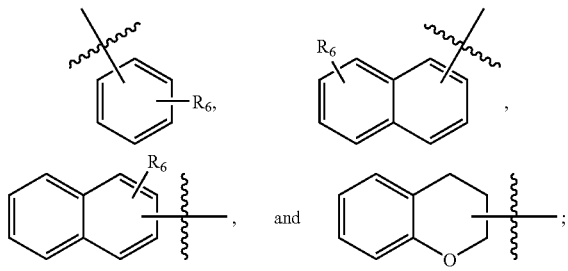

wherein:
$R_6$ is selected from the group consisting of H, $C_1$-$C_5$-alkyl, $C_1$-$C_5$-alkoxyl, OH, F, Cl, Br, and I.

10. The process of claim 4, wherein:
Z is butyl;
$R_3$ is H; and
$R_5$ is selected from the group consisting of

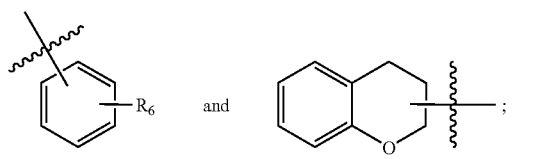

wherein:
$R_6$ is selected from the group consisting of H, $C_1$-$C_5$-alkyl, $C_1$-$C_5$-alkoxyl, OH, F, Cl, Br, and I.

11. The process of claim 4, wherein the compound, a stereochemical isomer of the compound, or a solvate or pharmaceutically acceptable salt of the compound or isomer according to Formula I is selected from the group consisting of:

(±)2-[4-[(Chroman-2-yl)methylamine]butyl]-1,3-dioxoperhydropyrrolo[1,2-c]imidazol;
(±)-2-[4-[(Chroman-2-yl)methylamine]butyl]-1,3-dioxoperhydroimidazo[1,5-b]thiazol;
(±)-2-[4-[(Chroman-2-yl)methylamine]butyl]-1,3-dioxoperhydroimidazo[1,5-c]-thiazol;
(±)-3-[4-[(Chroman-2-yl)methylamine]butyl]-2,4-dioxothiazolidin;
(±)-3-[5-[(Chroman-2-yl)methylamine]pentyl]-2,4-dioxothiazolidin;
(±)-3-[6-[(Chroman-2-yl)methylamine]hexyl]-2,4-dioxothiazolidin;
2-[4-[(Naphth-1-yl)methylamine]butyl]-1,3-dioxoperhydropyrrolo[1,2-c]imidazol;
2-[4-[(Naphth-2-yl)methylamine]butyl]-1,3-dioxoperhydropyrrolo[1,2-c]imidazol;
2-[4-[2-(Naphth-1-yl)ethylamine]butyl]-1,3-dioxoperhydropyrrolo[1,2-c]imidazol;
3-[4-[2-(Naphth-1-yl)ethylamine]butyl]-2,4-dioxothiazolidin;
2-[4-[2-(Naphth-2-yl)ethylamine]butyl]-1,3-dioxoperhydropyrrolo[1,2-c]imidazol;
2-[4-[2-(Phenoxy)ethylamine]butyl]-1,3-dioxoperhydropyrrolo[1,2-c]imidazol;
3-[4-[2-(Phenoxy)ethylamine]butyl]-2,4-dioxothiazolidin;
2-[4-[2-(Naphth-1-oxi)ethylamine]butyl]-1,3-dioxoperhydropyrrolo[1,2-c]imidazol;
3-[4-[2-(Naphth-1-oxi)ethylamine]butyl]-2,4-dioxothiazolidin;
2-[4-[(Benzimidazol-2-yl)methylamine]butyl]-1,3-dioxoperhydropyrrolo[1,2-c]imidazol;
2-[4-[(o-Methoxyphenyl)methylamine]butyl]-1,3-dioxoperhydropyrrolo[1,2-c]imidazol;
2-[4-[2-(o-Methoxyphenyl)ethylamine]butyl]-1,3-dioxoperhydropyrrolo[1,2-c]-imidazol;
2-[4-[3-(o-Methoxyphenyl)propylamine]butyl]-1,3-dioxoperhydropyrrolo[1,2-c]imidazol;
2-[4-[4-(o-Methoxyphenyl)butylamine]butyl]-1,3-dioxoperhydropyrrolol[1,2-c]imidazol; and
2-[3-[3-(o-Methoxyphenyl)propylamine]propyl]-1,3-dioxoperhydropyrrolo[1,2-c]imidazol.

12. The process of claim 4, wherein the compound, a stereochemical isomer of the compound, or a solvate or pharmaceutically acceptable salt of the compound or isomer according to Formula I is selected from the group consisting of 2-[4-[(chroman-2-yl)methylamino]butyl]-1,3-dioxoperhydropyrrolo[1,2-c]imidazole;
3-[4-[(chroman-2-yl)methylamino]butyl]-2,4-dioxothiazolidine;
3-[4-[(chroman-2-yl)methylamino]pentyl]-2,4-dioxothiazolidine;
3-[6-[(chroman-2-yl)methylamino]hexyl]-2,4-dioxothiazolidine;
2-[4-[2-(phenoxy)ethylamino]butyl]-1,3-dioxoperhydropyrrolo[1,2-c]imidazole; and
3-[4-[2-(phenoxy)ethylamino]butyl]-2,4-dioxothiazolidine.

13. The pharmaceutical composition of claim 6, wherein:
Z is $C_2$-$C_{10}$-alkyl; and
$R_5$ is selected from the group consisting of

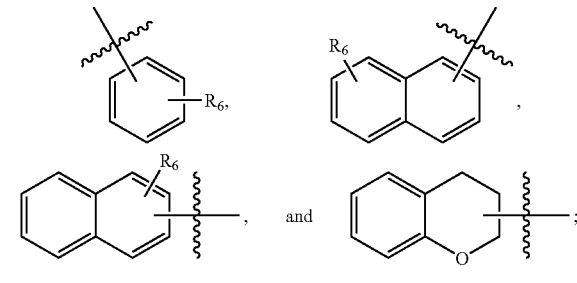

wherein:
$R_6$ is selected from the group consisting of H, $C_1$-$C_5$-alkyl, $C_1$-$C_5$-alkoxyl, OH, F, Cl, Br, and I.

14. The pharmaceutical composition of claim 6, wherein:
Z is butyl;
$R_3$ is H; and
$R_5$ is selected from the group consisting of

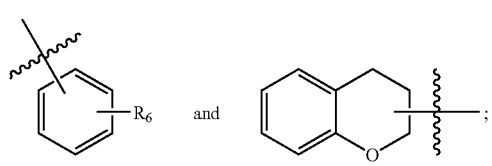

wherein:
R_6 is selected from the group consisting of H, $C_1$-$C_5$-alkyl, $C_1$-$C_5$-alkoxyl, OH, F, Cl, Br, and I.

15. The pharmaceutical composition of claim 6, wherein the compound, a stereochemical isomer of the compound, or a solvate or pharmaceutically acceptable salt of the compound or isomer according to Formula I is selected from the group consisting of
(±)2-[4-[(Chroman-2-yl)methylamine]butyl]-1,3-dioxoperhydropyrrolo[1,2-c]imidazol;
(±)-2-[4-[(Chroman-2-yl)methylamine]butyl]-1,3-dioxoperhydroimidazo[1,5-b]thiazol;
(±)-2-[4-[(Chroman-2-yl)methylamine]butyl]-1,3-dioxoperhydroimidazo[1,5-c]-thiazol;
(±)-3-[4-[(Chroman-2-yl)methylamine]butyl]-2,4-dioxothiazolidin;
(±)-3-[5-[(Chroman-2-yl)methylamine]pentyl]-2,4-dioxothiazolidin;
(±)-3-[6-[(Chroman-2-yl)methylamine]hexyl]-2,4-dioxothiazolidin;
2-[4-[(Naphth-1-yl)methylamine]butyl]-1,3-dioxoperhydropyrrolo[1,2-c]imidazol;
2-[4-[(Naphth-2-yl)methylamine]butyl]-1,3-dioxoperhydropyrrolo[1,2-c]imidazol;
2-[4-[2-(Naphth-1-yl)ethylamine]butyl]-1,3-dioxoperhydropyrrolo[1,2-c]imidazol;
3-[4-[2-(Naphth-1-yl)ethylamine]butyl]-2,4-dioxothiazolidin;
2-[4-[2-(Naphth-2-yl)ethylamine]butyl]-1,3-dioxoperhydropyrrolo[1,2-c]imidazol;
2-[4-[2-(Phenoxy)ethylamine]butyl]-1,3-dioxoperhydropyrrolo[1,2-c]imidazol;
3-[4-[2-(Phenoxy)ethylamine]butyl]-2,4-dioxothiazolidin;
2-[4-[2-(Naphth-1-oxi)ethylamine]butyl]-1,3-dioxoperhydropyrrolo[1,2-c]imidazol;
3-[4-[2-(Naphth-1-oxi)ethylamine]butyl]-2,4-dioxothiazolidin;
2-[4-[(Benzimidazol-2-yl)methylamine]butyl]-1,3-dioxoperhydropyrrolo[1,2-c]imidazol;
2-[4-[(o-Methoxyphenyl)methylamine]butyl]-1,3-dioxoperhydropyrrolo[1,2-c]imidazol;
2-[4-[2-(o-Methoxyphenyl)ethylamine]butyl]-1,3-dioxoperhydropyrrolo[1,2-c]-imidazol;
2-[4-[3-(o-Methoxyphenyl)propylamine]butyl]-1,3-dioxoperhydropyrrolo[1,2-c]imidazol;
2-[4-[4-(o-Methoxyphenyl)butylamine]butyl]-1,3-dioxoperhydropyrrolo[1,2-c]imidazol; and
2-[3-[3-(o-Methoxyphenyl)propylamine]propyl]-1,3-dioxoperhydropyrrolo[1,2-c]imidazol.

16. The pharmaceutical composition of claim 6, wherein the compound, a stereochemical isomer of the compound, or a solvate or pharmaceutically acceptable salt of the compound or isomer according to Formula I is selected from the group consisting of
2-[4-[(chroman-2-yl)methylamino]butyl]-1,3-dioxoperhydropyrrolo[1,2-c]imidazole;
3-[4-[(chroman-2-yl)methylamino]butyl]-2,4-dioxothiazolidine;
3-[5-[(chroman-2-yl)methylamino]pentyl]-2,4-dioxothiazolidine;
3-[6-[(chroman-2-yl)methylamino]hexyl]-2,4-dioxothiazolidine;
2-[4-[2-(phenoxy)ethylamino]butyl]-1,3-dioxoperhydropyrrolo[1,2-c]imidazole; and
3-[4-[2-(phenoxy)ethylamino]butyl]-2,4-dioxothiazolidine.

17. A method for the treatment of a pathological state in a subject in need of such treatment, wherein the method comprises administering to the subject a compound, a stereochemical isomer of the compound, or a solvate or pharmaceutically acceptable salt of the compound or isomer, wherein the compound corresponds in structure to Formula I:

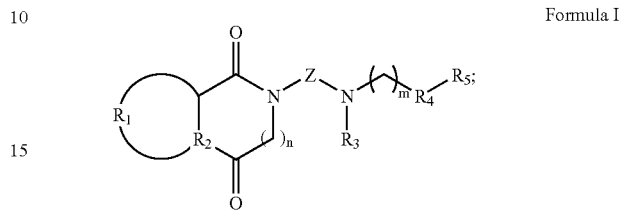

Formula I wherein:
R_2 is selected from the group consisting of N, NH and S; wherein
if R_2 is N, then R_1 is selected from the group consisting of —(CH_2)_3—, —(CH_2)_4—, —CH_2SCH_2—, and —SCH_2CH_2—;
if R_2 is S or NH, then R_1 is absent;
if R_2 is NH, then n is 1;
n has a value of zero or 1;
Z is selected from the group consisting of $C_2$-$C_{10}$-alkyl, $C_2$-$C_{10}$-alkenyl, and $C_2$-$C_{10}$-alkynl;
R_3 is selected from the group consisting of H, $C_1$-$C_{10}$-alkyl, aryl, and aralkyl;
m has a value of zero, 1, or 2;
R_4 is selected from the group consisting of O and CH_2;
R_5 is selected from the group consisting of

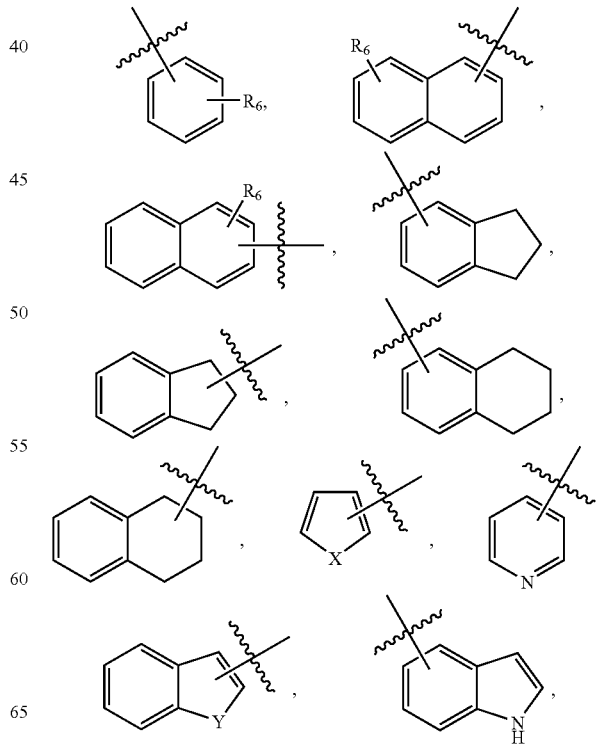

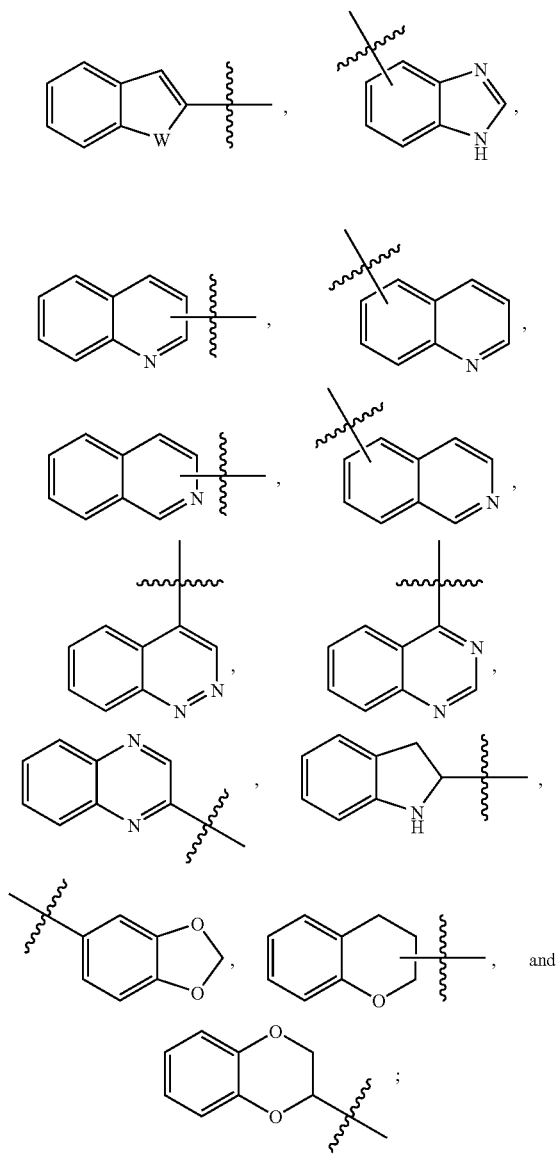

wherein:

R$_6$ is selected from the group consisting of H, $C_1$-$C_5$-alkyl, $C_1$-$C_5$-alkoxyl, OH, F, Cl, Br, and I;

X is selected from the group consisting of O, S, NH, and NCH$_3$;

Y is selected from the group consisting of O and NH;

W is selected from the group consisting of S and NH;

wherein a 5-HT$_{1A}$ agonist is indicated in the pathological state and the pathological state is selected from the group consisting of an anxiety disorder, depression and a mixed disorder of anxiety and depression.

18. A method to provide neuroprotection to a subject in need thereof comprising administering to the subject a neuroprotective amount of a compound, a stereochemical isomer of the compound, or solvate or pharmaceutically acceptable salt of the compound or isomer, wherein the compound corresponds in structure to Formula I:

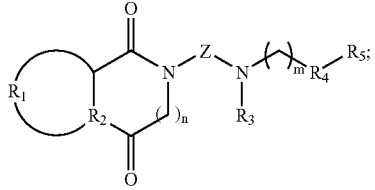

Formula I wherein:

R$_2$ is selected from the group consisting of N, NH and S; wherein if R$_2$ is N, then R$_1$ is selected from the group consisting of —(CH$_2$)$_3$—, —(CH$_2$)$_4$—, —CH$_2$SCH$_2$, and —SCH$_2$CH$_2$—;

if R$_2$ is S or NH, then R$_1$ is absent;

if R$_2$ is NH, then n is 1;

n has a value of zero or 1;

Z is selected from the group consisting of $C_2$-$C_{10}$-alkyl, $C_2$-$C_{10}$-alkenyl, and $C_2$-$C_{10}$-alkynyl;

R$_3$ is selected from the group consisting of H, $C_1$-$C_{10}$-alkyl, aryl, and aralkyl;

m has a value of zero, 1, or 2;

R$_4$ is selected from the group consisting of O and CH$_2$;

R$_5$ is selected from the group consisting of

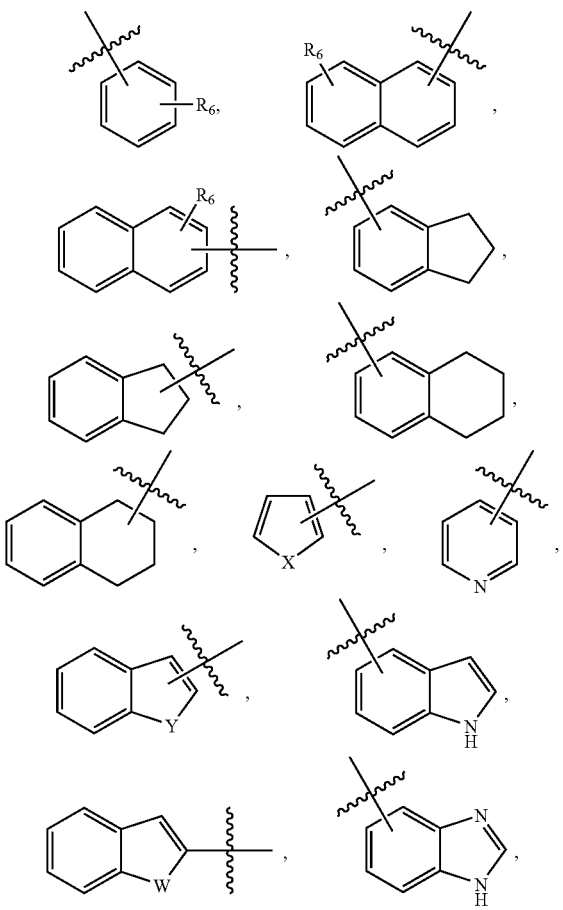

-continued

[structures]

wherein:
R$_6$ is selected from the group consisting of H, C$_1$-C$_5$-alkyl, C$_1$-C$_5$-alkoxyl, OH, F, Cl, Br, and I;
X is selected from the group consisting of O, S, NH, and NCH$_3$;
Y is selected from the group consisting of O and NH;
W is selected from the group consisting of S and NH.

19. The method according to claim 18 wherein the neuroprotection provided comprises the treatment of cerebral damage produced by thromboembolic stroke or cranium-brain traumatic injuries.

20. The compound, a stereochemical isomer of the compound, or a solvate or pharmaceutically acceptable salt of the compound or isomer according to claim 1 wherein the compound corresponds in structure to Formula Ib:

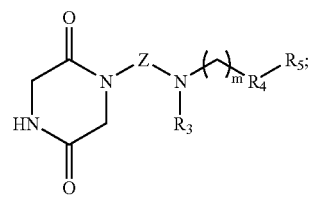

Formula Ib wherein the definition of n, Z, R$_3$, m, R$_4$ and R$_5$ are identical to those in claim 1.

21. The compound, a stereochemical isomer of the compound, or a solvate or pharmaceutically acceptable salt of the compound or isomer according to claim 1 wherein the compound corresponds in structure to Formula Ic:

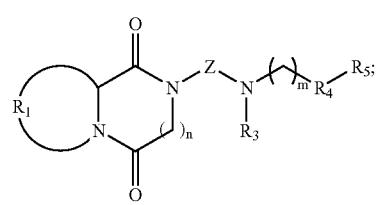

Formula Ic wherein the definition of Z, R$_3$, m, R$_4$ and R$_5$ are identical to those in claim 1.

22. The compound, a stereochemical isomer of the compound, or a solvate or phannaceutically acceptable salt of the compound or isomer according to claim 1 wherein the compound corresponds in structure to Formula Id:

Formula Id wherein the definition of R$_1$, n, Z, R$_3$, m, R$_4$ and R$_5$ are identical to those in claim 1.

23. A compound, a stereochemical isomer of the compound, or a solvate or pharmaceutically acceptable salt of the compound or isomer, wherein the compound corresponds in structure to Formula I:

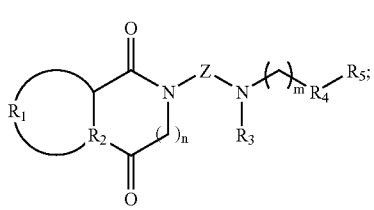

Formula I wherein:
R$_2$ is selected from the group consisting of N and S; wherein
  if R$_2$ is N, then R$_1$ is selected from the group consisting of —(CH$_2$)$_3$—, —(CH$_2$)$_4$—, —CH$_2$SCH$_2$, and —SCH$_2$CH$_2$—;
  if R$_2$ is S, then R$_1$ is absent;
n has a value of zero or 1;
Z is selected from the group consisting of C$_2$-C$_{10}$-alkyl, C$_2$-C$_{10}$-alkenyl, and C$_2$-C$_{10}$-alkynyl;
R$_3$ is selected from the group consisting of H, C$_1$-C$_{10}$-alkyl, aryl, and aralkyl;
m has a value of zero, 1, or 2;

$R_4$ is selected from the group consisting of O and $CH_2$;
$R_5$ is selected from the group consisting of
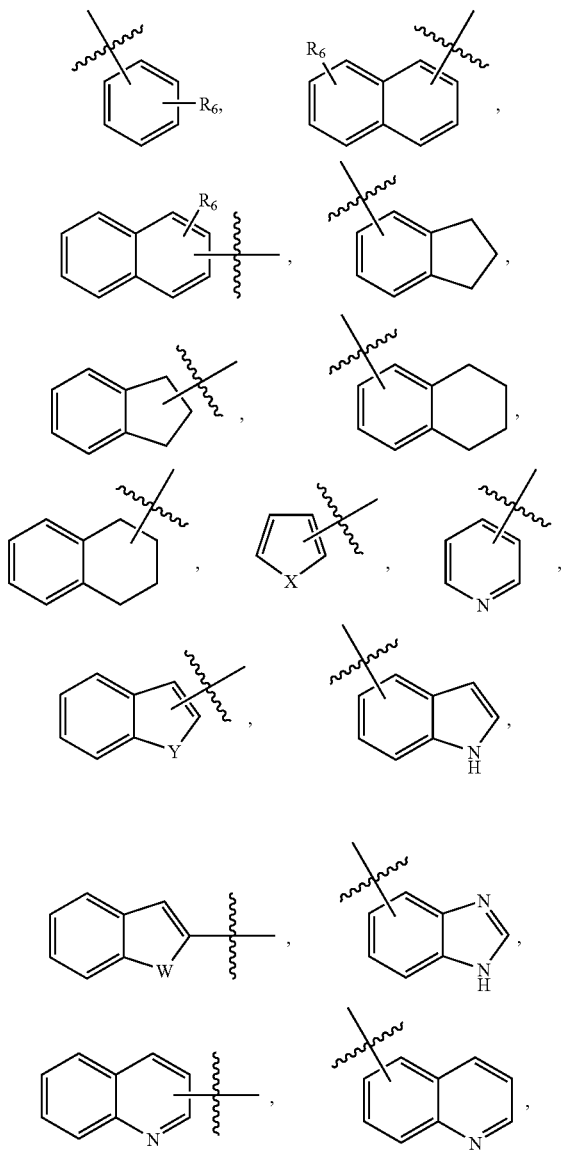
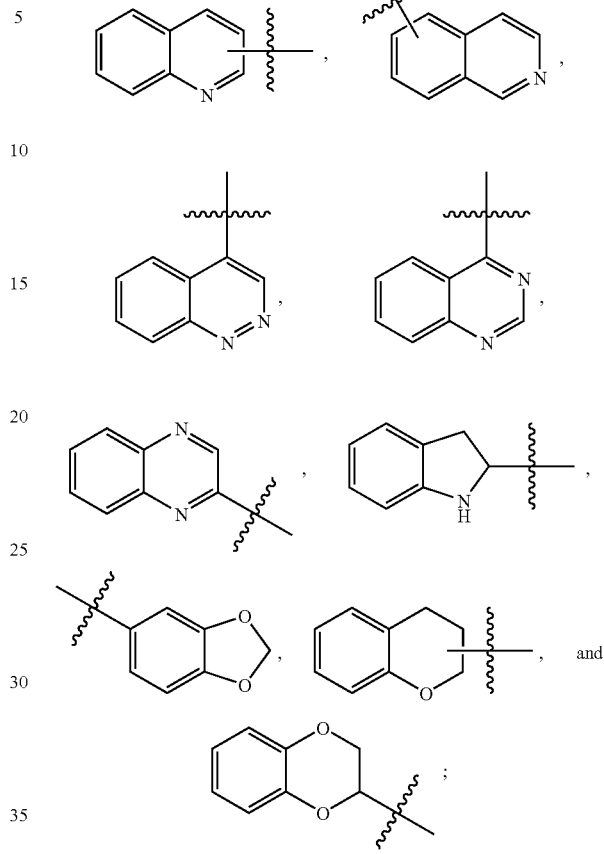
wherein:
$R_6$ is selected from the group consisting of H, $C_1$-$C_5$-alkyl, $C_1$-$C_5$-alkoxyl, OH, F, Cl, Br, and I;
X is selected from the group consisting of O, S, NH, and $NCH_3$;
Y is selected from the group consisting of O and NH;
W is selected from the group consisting of S and NH.
* * * * *